(12) United States Patent
Pelcman et al.

(10) Patent No.: US 11,168,069 B2
(45) Date of Patent: Nov. 9, 2021

(54) HETEROCYCLYLSULFONYL-SUBSTITUTED PYRIDINES AND THEIR USE IN THE TREATMENT OF CANCER

(71) Applicant: Oblique Therapeutics AB, Gothenburg (SE)

(72) Inventors: Benjamin Pelcman, Stockholm (SE); William Stafford, Farsta (SE)

(73) Assignee: Oblique Therapeutics AB, Gothenburg (SE)

( * ) Notice: Subject to any disclaimer, the term of this patent is extended or adjusted under 35 U.S.C. 154(b) by 0 days.

(21) Appl. No.: 16/483,961

(22) PCT Filed: Feb. 7, 2018

(86) PCT No.: PCT/GB2018/050345
§ 371 (c)(1),
(2) Date: Aug. 6, 2019

(87) PCT Pub. No.: WO2018/146471
PCT Pub. Date: Aug. 16, 2018

(65) Prior Publication Data
US 2020/0024255 A1 Jan. 23, 2020

Related U.S. Application Data

(60) Provisional application No. 62/594,784, filed on Dec. 5, 2017, provisional application No. 62/455,644, filed on Feb. 7, 2017.

(51) Int. Cl.
 C07D 401/12 (2006.01)
 A61P 35/00 (2006.01)
 C07D 407/12 (2006.01)

(52) U.S. Cl.
 CPC ............ *C07D 401/12* (2013.01); *A61P 35/00* (2018.01); *C07D 407/12* (2013.01)

(58) Field of Classification Search
 CPC .................................................. C07D 401/12
 USPC .......................................................... 546/297
 See application file for complete search history.

(56) References Cited

U.S. PATENT DOCUMENTS

| | | | |
|---|---|---|---|
| 4,456,469 | A | 6/1984 | Adams, Jr. |
| 4,966,974 | A | 10/1990 | Klausener et al. |
| 8,609,851 | B2 | 12/2013 | Yang et al. |
| 8,946,418 | B1 | 2/2015 | Haddad et al. |
| 10,899,710 | B2 | 1/2021 | Arner et al. |
| 2005/0009871 | A1 | 1/2005 | Ramesh et al. |
| 2005/0250816 | A1 | 11/2005 | Piotrowski et al. |
| 2006/0019967 | A1 | 1/2006 | Wu et al. |
| 2013/0203738 | A1 | 8/2013 | Nishimura et al. |
| 2020/0024233 | A1 | 1/2020 | Pelcman et al. |
| 2020/0223819 | A1 | 7/2020 | Pelcman et al. |
| 2020/0239417 | A1 | 7/2020 | Pelcman et al. |

FOREIGN PATENT DOCUMENTS

| | | |
|---|---|---|
| CN | 102206172 A | 10/2011 |
| CN | 104672214 A | 6/2015 |
| CN | 104987324 A | 10/2015 |
| CN | 105085483 A | 11/2015 |
| CN | 105503827 A | 4/2016 |
| DE | 19531148 A1 | 2/1997 |
| EP | 0031173 A1 | 7/1981 |
| EP | 35893 A2 | 9/1981 |
| EP | 220857 A1 | 5/1987 |
| EP | 0337560 A2 | 10/1989 |
| EP | 2366691 A1 | 9/2011 |
| RU | 2201922 C2 | 4/2003 |
| WO | 1995/29897 A1 | 11/1995 |
| WO | 1997/08147 A1 | 3/1997 |
| WO | 1998/54139 A1 | 12/1998 |
| WO | 1999/010320 A1 | 3/1999 |
| WO | 1999/017777 A1 | 4/1999 |
| WO | 1999/18096 A1 | 4/1999 |
| WO | 1999/36391 A1 | 7/1999 |
| WO | 2001/064642 A2 | 9/2001 |
| WO | 2003/051366 A2 | 6/2003 |
| WO | 2003/068744 A1 | 8/2003 |
| WO | 2003/093250 A2 | 11/2003 |
| WO | 2004/005323 A2 | 1/2004 |
| WO | 2005/007621 A2 | 1/2005 |
| WO | 2005/121121 A2 | 12/2005 |

(Continued)

OTHER PUBLICATIONS

Arner et al., Physiological functions of thioredoxin and thioredoxin reductase. Eur J Biochem. Oct. 2000;267(20):6102-9.

(Continued)

*Primary Examiner* — Taofiq A Solola
(74) *Attorney, Agent, or Firm* — McCarter & English, LLP; Steven G. Davis; Mei Bai

(57) ABSTRACT

There is provided compounds of formula I (I) or pharmaceutically-acceptable salts thereof, wherein L, $R^1$, $R^2$, $R^3$ and X have meanings provided in the description, which compounds are useful in the treatment of cancers.

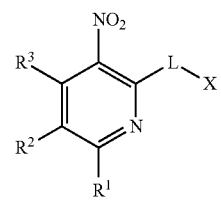

(I)

15 Claims, No Drawings

(56) References Cited

FOREIGN PATENT DOCUMENTS

| WO | 2006/059149 A1 | 6/2006 |
| WO | 2006/083692 A2 | 8/2006 |
| WO | 2006/095205 A1 | 9/2006 |
| WO | 2007/076875 A2 | 7/2007 |
| WO | 2007/124546 A1 | 11/2007 |
| WO | 2009/012283 A1 | 1/2009 |
| WO | 2010/138820 A2 | 12/2010 |
| WO | 2011/022440 A9 | 2/2011 |
| WO | 2012/025638 A1 | 3/2012 |
| WO | 2013/119931 A1 | 8/2013 |
| WO | 2015/081813 A1 | 6/2015 |
| WO | 2017/027359 A1 | 2/2017 |

OTHER PUBLICATIONS

Arner, Focus on mammalian thioredoxin reductases—important selenoproteins with versatile functions. Biochim Biophys Acta. Jun. 2009;1790(6):495-526.

Becker et al., Thioredoxin reductase as a pathophysiological factor and drug target. Eur J Biochem. Oct. 2000;267(20):6118-25.

Cox et al., The thioredoxin reductase inhibitor auranofin triggers apoptosis through a Bax/Bak-dependent process that involves peroxiredoxin 3 oxidation. Biochem Pharmacol. Oct. 30, 2008;76(9):1097-109.

Fath et al., Enhancement of carboplatin-mediated lung cancer cell killing by simultaneous disruption of glutathione and thioredoxin metabolism. Clin Cancer Res. Oct. 1, 2011;17(19):6206-17.

Harris et al., Glutathione and thioredoxin antioxidant pathways synergize to drive cancer initiation and progression. Cancer Cell. Feb. 9, 2015;27(2):211-22.

Hashemy et al., Motexafin gadolinium, a tumor-selective drug targeting thioredoxin reductase and ribonucleotide reductase. J Biol Chem. Apr. 21, 2006;281(16):10691-7.

Jamoulle et al., Preparation et proprietes protozoocides de sulfures et sulfones hétérocycliques. Ann Pharmaceutiques francaises. 1983;41(1):61-8.

Jamoulle et al., Synthese de Quelques Alkylsulfonyl-2 Pyridines Substituees en Position 3. J Pharm Belg. 1975;30(2):114-20.

Krishnamurthy et al., Gold(I)-mediated inhibition of protein tyrosine phosphatases: a detailed in vitro and cellular study. J Med Chem. Aug. 14, 2008;51(15):4790-5.

Lillig et al., Glutaredoxin systems. Biochim Biophys Acta. Nov. 2008;1780(11):1304-17.

Luo et al., Principles of cancer therapy: oncogene and non-oncogene addiction. Cell. Mar. 6, 2009;136(5):823-37.

Mandal et al., Loss of thioredoxin reductase 1 renders tumors highly susceptible to pharmacologic glutathione deprivation. Cancer Res. Nov. 15, 2010;70(22):9505-14.

Moshchitskii et al., Competitive Nucleophilic Substitution Reactions of Methysulfonyl and Nitro Derivatives of Polychloropyridines. Khimiya Geterotsiklicheskikh Soedinenii. Jun. 1975;6:802-6.

Prigge et al., Hepatocyte DNA replication in growing liver requires either glutathione or a single allele of txnrd1. Free Radic Biol Med. Feb. 15, 2012;52(4):803-10.

Rigobello et al., Effect of auranofin on the mitochondrial generation of hydrogen peroxide. Role of thioredoxin reductase. Free Radic Res. Jul. 2005;39(7):687-95.

Talik et al., Synthesis of Some Sulfoderivatives of Pyridine. Polish Journal of Chemistry. 1978;52:163-70.

Talik et al., Synteza Niektorych Siarkowych Pochodnych 3,5-Dinitro-6-Metylopirydyny. Prace Naukowe Akademii Ekonomicznej We Wroclawiu. 1984;255:137-144.

Trachootham et al., Targeting cancer cells by ROS-mediated mechanisms: a radical therapeutic approach? Nat Rev Drug Discov. Jul. 2009;8(7):579-91.

Zhang et al., Thioredoxin reductase inhibitors: a patent review. Expert Opin Ther Pat. May 2017;27(5):547-556.

Takahashi et al., Sulfur-containing pyridine derivatives. LVI. Smiles rearrangement of pyridine derivatives and synthesis of benzopyrido- and dipyrido-1,4-thiazine derivatives. 4. Chem Pharm Bull (Tokyo). Aug. 1958;6(4):369-73.

International Search Report and Written Opinion for Application No. PCT/GB2018/050345, dated May 28, 2018, 10 pages.

Belikov, Pharmaceutical Chemistry. Medpress-inform. pp. 27-29, (2007).

Braun et al., Synthesis and biological evaluation of optimized inhibitors of the mitotic kinesin Kif18A. ACS Chem Biol. Feb. 20, 2015;10(2):554-60.

Cannon, Analog Design. Burger's Medicinal Chemistry and Drug Discovery, Fifth Edition, vol. I: Principles and Practice. Wiley-Interscience. Chapter 19, pp. 783-802, (1995).

Dorwald, Side Reactions in Organic Synthesis, A Guide to Successful Synthesis Design. Wiley-VCH Verlag GmbH & Co. KGaA. 37 pages, (2005).

El-Zahara et al., Mass Spectral Study of Some Phenyl-mono and Dinitropyridyl Sulfide, Ether, Amine and Sulfone Derivatives. Rapid Communications in Mass Spectrometry. 1997;11:316-320.

Lu et al., Structure-based drug design and structural biology study of novel nonpeptide inhibitors of severe acute respiratory syndrome coronavirus main protease. J Med Chem. Aug. 24, 2006;49(17):5154-61.

Maki et al., Studies of Rearrangement Reaction XIII. Smiles Rearrangement on Pyridine Derivatives. Gifu Yakka Daigaku Kiyo. 1965;15:31-33.

Maki et al., Studies of rearrangement reactions. X. Smiles rearrangement on pyridine derivatives. 7. Yakugaku Zasshi. May 1965;85(5):429-36.

Maloney et al., A practical, one-pot synthesis of sulfonylated pyridines. Org Lett. Jan. 7, 2011;13(1):102-5.

Moss, IUPAC, Pure and Applied Chemistry. 1995;67:1314, 1330.

Robison et al., 7-Azaindole. VI. Preparation of 5- and 6-Substituted 7-azaindoles. J Am Chem Soc. 1959;81:743-747.

Rowe, Alcohol. Handbook of Pharmaceutical Excipients, Sixth Edition. Pharmaceutical Press. pp. 17-19, (2009).

STN RN 1087745-45-6, Pyridine, 5-methyl-3-nitro-2-(phenylsulfonyl)—5 pages, Dec. 21, 2008.

STN RN 1258786-29-6, 6-Methoxy-2-[(4-methylphenyl)sulfonyl]-3-nitropyridine, 6 pages, Jan. 7, 2011.

STN RN 188429-02-9, Pyridine, 3-nitro-2-(phenylsulfonyl)—5 pages, Apr. 18, 1997.

STN RN 246020-68-8, Pyridine, 2-[(4-chlorophenyl)sulfonyl]-6-methoxy-3-nitro—2 pages, Nov. 3, 1999.

STN RN 3573-15-7, Acetamide, N-[2-[(5-chloro-3-nitro-2-pyridinyl)sulfonyl]phenyl]—5 pages, Nov. 16, 1984.

STN RN 477871-39-9, Pyridine, 2-[(4-methylphenyl)sulfonyl]-3-nitro—2 pages, Dec. 31, 2002.

STN RN 97420-49-0, Pyridine, 2-methyl-3, 5-dinitro-6-(phenylsulfonyl)—3 pages, Aug. 4, 1985.

Storey, Benzyl Alcohol. Handbook of Pharmaceutical Excipients, Sixth Edition. Pharmaceutical Press, London. Raymond C. Rowe (Ed.). pp. 64-66, (2009).

Takayama et al., Diels-Alder Reaction of 3-(2-Pyridylsulfinyl)Acrylates—The Enhancement of the Reactivity and the Diastereoelectivity by the Introduction of Electron-withdrawing Substituents on the Pyridine Ring. Hetercycles. 1986;24(8):2137-40.

Trankle et al., Green Chemical Synthesis of 2-Benzenesulfonyl-pyridine and Related Derivatives. Organic Process Research & Development. 2007;11:913-917.

Venkatesh et al., Role of the development scientist in compound lead selection and optimization. J Pharm Sci. Feb. 2000;89(2):145-54.

Wang et al., Discovery of nitropyridine derivatives as potent HIV-1 non-nucleoside reverse transcriptase inhibitors via a structure-based core refining approach. Eur J Med Chem. Apr. 9, 2014;76:531-8.

Wikipedia, *Staphylococcus aureus*. Retrieved online at: https://en.wikipedia.org/w/index.php?title=Staphylococcus_aureus?oldid=742752735. 9 pages, (2020).

Russian Office Action for Application No. 2018107879, dated Feb. 25, 2020, 7 pages.

HETEROCYCLYLSULFONYL-SUBSTITUTED PYRIDINES AND THEIR USE IN THE TREATMENT OF CANCER

This application is a 371 of International Application No. PCT/GB2018/050345, filed on Feb. 7, 2018, which claims the benefit of U.S. Provisional Application No. 62/594,784, filed on Dec. 5, 2017, and to U.S. Provisional Application No. 62/455,644, filed on Feb. 7, 2017. The entire contents of these applications are incorporated herein by reference in their entirety.

FIELD OF THE INVENTION

The present invention relates to novel compounds and compositions, and their use in the treatment of cancer. In particular, the invention relates to novel compounds, compositions and methods for the treatment of cancers through specific and potent inhibition of thioredoxin reductase with minimal inhibition of glutathione reductase.

BACKGROUND OF THE INVENTION

The listing or discussion of an apparently prior-published document in this specification should not necessarily be taken as an acknowledgement that the document is part of the state of the art or is common general knowledge.

Although the increased understanding of the role of oncogenes, and the development of new anticancer treatments and diagnosis, have improved the life expectancy of cancer patients, there is still a high medical need to find more effective and less toxic treatments for cancers, such as breast cancer, head and neck cancer, melanoma, glioblastoma, leukaemia, and colon and lung cancer.

It is well known that excessive production of reactive oxygen species is a common feature of cancer cells due to their distorted metabolism and exaggerated replicative drive. Cancer cells are able to survive their unnaturally high production of reactive oxygen species through concomitant upregulation of robust antioxidant defence mechanisms.

Radiotherapy and chemotherapy protocols compete against antioxidant defence mechanisms, further increasing reactive oxygen species levels beyond adapted thresholds through targeting of multiple cellular compartments and targets. Thus, sensitization of cancer cells to their endogenous reactive oxygen species production can additionally induce cancer cell death. In contrast, normal cells have reserved capacity to combat oxidative stress. With this in mind, it has been suggested that if reactive oxygen species levels could be further increased, or the cellular defences against reactive oxygen species could be deliberately impaired, these systems may serve to allow for a possible therapeutic mechanism of action for anticancer therapy (Luo, J., Solimini, N. L. & Elledge, S. J., Cell, 136, 823 (2009); Trachootham, D., Alexandre, J. & Huang, P., Nat Rev Drug Discov, 8, 579 (2009)).

Increased tolerance to oxidative stress of cancer cells can occur through activation of the two major antioxidant systems in human and other mammals: the glutathione and thioredoxin systems. Concomitant inhibition of the glutathione and thioredoxin systems therefore has been proposed as a mechanism for anticancer activity (Harris, I. S., et al., *Cancer Cell* 27, 211 (2015); Mandal, P. K., et al., *Cancer Res*, 70, 9505-9514 (2010); Fath, M. A., Ahmad, I. M., Smith, C. J., Spence, J. & Spitz, D. R., *Clin Cancer Res.*, 17, 6206 (2011)).

Cytosolic thioredoxin reductase is a key enzyme for the whole cytosolic thioredoxin system, which in turn is responsible for a cascade of signalling events and antioxidant activities (Arnér, E. S. J., *Biochim Biophys Acta*, 1790, 495-526 (2009)). A high expression level of cytosolic thioredoxin reductase in various cancers correlates to a more severe cancer phenotype, chemotherapeutic drug resistance, and poor prognosis.

However, as normal, non-cancerous cells require either the glutathione or the thioredoxin systems for survival (Arnér, E. S. & Holmgren, A., *Eur J Biochem*, 267, 6102 (2000); Lillig, C. H., Berndt, C. & Holmgren, A., *Biochim Biophys Acta*, 1780, 1304 (2008); Prigge, J. R., et al., *Free Radic Biol Med*, 52, 803 (2012)), it is difficult to therapeutically target both of these antioxidant systems without triggering major unwanted toxicities.

It has been suggested that several chemotherapeutic protocols for anticancer treatment involve inhibition of cytosolic thioredoxin reductase together with other components of the cell (Becker, K. et al. *Eur. J. Biochem.*, 267, 6118 (2000)). For example, motexafin gadolinium, marketed as a radiosensitizing drug and thioredoxin reductase inhibitor, is also a potent ribonucleotide reductase inhibitor (Hashemy, S. I., Ungerstedt, J. S., Zahedi Avval, F. & Holmgren, A., *J Biol Chem*, 281, 10691 (2006)). Auranofin, a potent thioredoxin reductase inhibitor, concomitantly localizes to and damages the mitochondria (Cox, A. G., Brown, K. K., Arnér, E. S. & Hampton, M. B., *Biochem Pharmacol*, 76, 1097-1109 (2008); Krishnamurthy, D., et al., *J Med Chem*, 51, 4790 (2008); Rigobello, M. P., Folda, A., Baldoin, M. C., Scutari, G. & Bindoli, A., *Free Radic Res*, 39, 687 (2005)).

The structure and function of thioredoxin reductase, biological effects associated with its inhibition, such as in its potential as a mechanism for cancer treatment, and compounds previously disclosed as potential inhibitors are reviewed in Zhang, B. et al., *Expert Opinion on Therapeutic Patents* (2016).

The present innovation relates to the development and usage of novel compounds specifically and potently targeting cytosolic thioredoxin reductase, without targeting the closely related flavoprotein glutathione reductase that supports the function of the glutathione system, as a means of obtaining a new efficient anticancer treatment that at the same time presents limited toxic side effects.

In particular, the inventors have unexpectedly found that novel, pyridinyl sulfone compounds may achieve highly selective inhibition of cytosolic thioredoxin reductase by acting as strongly-binding (and, in some cases, effectively irreversible) inhibitors of the enzyme without causing significant inhibition of glutathione reductase.

Specifically, by potently inhibiting thioredoxin reductase selectively over glutathione reductase, the novel pyridinyl sulfones have the potential to be effective against cancer forms having dysfunctional redox status, with minimal general toxic effects to normal cells. Such inhibitors may also be a suitable adjuvant therapy to be used in conjunction with radiotherapies or other chemotherapeutic approaches. Based on these surprising results, the present invention aims to provide new treatments for cancers.

International patent application WO 2005/007621 describes certain compounds as ubiquitin ligase inhibitors and their use in treating cell proliferative diseases. However, none of exemplified compounds contain a nitro substituted pyridine that is linked via a sulfonyl moiety to an optionally substituted heterocyclyl group (as defined herein).

International patent application WO 95/29897 describes certain ($H^+/K^+$)ATPase inhibitors and their use in treating viral infections. However, none of the exemplified compounds contain a nitro substituted pyridine linked via a sulfonyl moiety to an optionally substituted heterocyclyl group.

International patent application WO 98/54139 describes a process for the preparation of certain pyridines. However, none of the exemplified compounds contain a nitro substituted pyridine linked via a sulfonyl moiety to an optionally substituted heterocyclyl group.

International patent applications WO 99/18096 and WO 99/017777 describe certain compounds and their use in treating conditions such as cancer. However, none of the exemplified compounds contain a nitro substituted pyridine linked via a sulfonyl moiety to an optionally substituted heterocyclyl group.

International patent application WO 01/064642 describes certain compounds and their use in treating coagulation disorders. However, none of the exemplified compounds contain a nitro substituted pyridine linked via a sulfonyl moiety to an optionally substituted heterocyclyl group.

DETAILED DESCRIPTION OF THE INVENTION

It has now been found that certain nitro substituted pyridines linked via a sulfonyl moiety to an optionally substituted heterocyclyl group, as defined herein, have surprising properties which render such compounds useful in the treatment of cancers.

Compounds of the Invention

In a first aspect of the invention, there is provided a compound of formula I

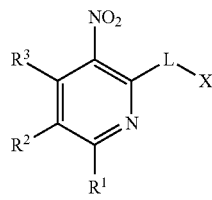

(I)

or a pharmaceutically acceptable salt thereof, wherein:
L represents $-S(O)_n-$;
n represents 2 or 1;
X represents heterocyclyl, connected to L via a carbon atom, and optionally substituted by one or more groups independently selected from Y;
$R^1$, $R^2$ and $R^3$ each independently represent H, halo, $R^{a1}$, $-CN$, $-A^{a1}-C(Q^{a1})R^{b1}$, $-A^{b1}-C(Q^{b1})N(R^{c1})R^{d1}$, $-A^{c1}-C(Q^{c1})OR^{e1}$, $-A^{d1}-S(O)_pR^{f1}$, $-A^{e1}-S(O)_pN(R^{g1})R^{h1}$, $-A^{f1}-S(O)_pOR^{i1}$, $-N_3$, $-N(R^{j1})R^{k1}$, $-N(H)CN$, $-NO_2$, $-ONO_2$, $-OR^{l1}$ or $-SR^{m1}$;
each $A^{a1}$ to $A^{f1}$ independently represents a single bond, $-N(R^{p1})-$ or $-O-$;
each $Q^{a1}$ to $Q^{c1}$ independently represents $=O$, $=S$, $=NR^{n1}$ or $=N(OR^{o1})$;
each $R^{a1}$ and $R^{f1}$ independently represents $C_{1-6}$ alkyl, $C_{2-6}$ alkenyl or $C_{2-6}$ alkynyl each optionally substituted by one or more groups independently selected from $G^{1a}$, heterocyclyl optionally substituted by one or more groups independently selected from $G^{1b}$, aryl optionally substituted by one or more groups independently selected from $G^{1c}$, or heteroaryl optionally substituted by one or more groups independently selected from $G^{1d}$;

each $R^{b1}$, $R^{c1}$, $R^{d1}$, $R^{e1}$, $R^{g1}$, $R^{h1}$, $R^{i1}$, $R^{j1}$, $R^{k1}$, $R^{l1}$, $R^{m1}$, $R^{n1}$, $R^{o1}$, and $R^{p1}$ independently represents H, $C_{1-6}$ alkyl, $C_{2-6}$ alkenyl or $C_{2-6}$ alkynyl each optionally substituted by one or more groups independently selected from $G^{1a}$, heterocyclyl optionally substituted by one or more groups independently selected from $G^{1b}$, aryl optionally substituted by one or more groups independently selected from $G^{1c}$, or heteroaryl optionally substituted by one or more groups independently selected from $G^{1d}$; or any of $R^{c1}$ and $R^{d1}$, $R^{g1}$ and $R^{h1}$ and/or $R^{j1}$ and $R^{k1}$ are linked together to form, together with the nitrogen atom to which they are attached, a 3- to 6-membered ring, which ring optionally contains one further heteroatom and which ring optionally is substituted by one or more groups independently selected from $G^{1b}$, $C_{1-3}$ alkyl, $C_{2-3}$ alkenyl or $C_{2-3}$ alkynyl each optionally substituted by one or more $G^{1a}$, and $=O$;

each $G^{1a}$ and $G^{1b}$ independently represents halo, $-CN$, $-N(R^{a2})R^{b2}$, $-OR^{c2}$, $-SR^{d2}$ or $=O$;

each $R^{a2}$, $R^{b2}$, $R^{c2}$ and $R^{d2}$ independently represents H or $C_{1-6}$ alkyl, $C_{2-6}$ alkenyl or $C_{2-6}$ alkynyl each optionally substituted by one or more fluoro; or $R^{a2}$ and $R^{b2}$ are linked together to form, along with the nitrogen atom to which they are attached, a 3- to 6-membered ring, which ring optionally contains one further heteroatom and which ring optionally is substituted by one or more groups independently selected from fluoro and $C_{1-3}$ alkyl, $C_{2-3}$ alkenyl or $C_{2-3}$ alkynyl each optionally substituted by one or more fluoro;

each Y independently represents halo, $R^{a3}$, $-CN$, $-A^{a2}-C(Q^{a2})R^{b3}$, $-A^{b2}-C(Q^{b2})N(R^{c3})R^{d3}$, $-A^{c2}-O(Q^{c2})OR^{e3}$, $-A^{d2}-S(O)_qR^{f3}$, $-A^{e2}-S(O)_qN(R^{g3})R^{h3}$, $-A^{f2}-S(O)_qR^{i3}$, $-N_3$, $-N(R^{j3})R^{k3}$, $-N(H)CN$, $-NO_2$, $-ONO_2$, $-SR^{m3}$ or $=O$;

each $Q^{a2}$ to $Q^{c2}$ independently represents $=O$, $=S$, $=NR^{n3}$ or $=N(OR^{o3})$;

each $A^{a2}$ to $A^{f2}$ independently represents a single bond, $-N(R^{p3})-$ or $-O-$;

each $R^{a3}$ and $R^{f3}$ independently represents $C_{1-6}$ alkyl, $C_{2-6}$ alkenyl or $C_{2-6}$ alkynyl each optionally substituted by one or more groups independently selected from $G^{2a}$, heterocyclyl optionally substituted by one or more groups independently selected from $G^{2b}$, aryl optionally substituted by one or more groups independently selected from $G^{2c}$, or heteroaryl optionally substituted by one or more groups independently selected from $G^{2d}$;

each $R^{b3}$, $R^{c3}$, $R^{d3}$, $R^{e3}$, $R^{g3}$, $R^{h3}$, $R^{i3}$, $R^{j3}$, $R^{k3}$, $R^{l3}$, $R^{m3}$, $R^{n3}$, $R^{o3}$ and $R^{p3}$ independently represents H, $C_{1-6}$ alkyl, $C_{2-6}$ alkenyl or $C_{2-6}$ alkynyl each optionally substituted by one or more groups independently selected from $G^{2a}$, heterocyclyl optionally substituted by one or more groups independently selected from $G^{2b}$, aryl optionally substituted by one or more groups independently selected from $G^{2c}$, or heteroaryl optionally substituted by one or more groups independently selected from $G^{2d}$; or any two $R^{c3}$ and $R^{d3}$, $R^{g3}$ and $R^{h3}$ and/or $R^{j3}$ and $R^{k3}$ are linked together to form, along with the nitrogen atom to which they are attached, a 3- to 6-membered ring, which ring optionally contains one further heteroatom and which ring optionally is substituted by one or more groups independently selected from heterocyclyl optionally substituted by one or more groups independently selected from $G^{2b}$, aryl optionally substituted by one or more groups independently selected from $G^{2c}$, or heteroaryl optionally substituted by one or more groups independently selected from $G^{2d}$, and $=O$;

each $G^{2a}$ independently represents halo, —CN, —N($R^{j4}$)$R^{k4}$, —OR$^{l4}$, —SR$^{m4}$ or =O;

each $G^{2b}$ independently represents halo, $R^{a4}$, —CN, —N($R^{j4}$)$R^{k4}$, —OR$^{l4}$, —SR$^{m4}$ or =O;

each $G^{2c}$ and $G^{2d}$ independently represents halo, $R^{a4}$, —CN, -$A^{a3}$-C($Q^{a4}$)$R^{b4}$, -$A^{b3}$-C($Q^{b3}$)N($R^{c4}$)$R^{d4}$, -$A^{c3}$-C($Q^{c3}$)OR$^{e4}$, -$A^{d3}$-S(O)$_q$$R^{f4}$, -$A^{e3}$-S(O)$_q$N($R^{g4}$)$R^{h4}$, -$A^{f3}$-S(O)$_q$OR$^{i4}$, —N$_3$, —N($R^{j4}$)$R^{k4}$, —N(H)CN, —NO$_2$, —ONO$_2$, —OR$^{l4}$ or —SR$^{m4}$;

each $Q^{a3}$ to $Q^{c3}$ independently represents =O, =S, =NR$^{n4}$ or =N(OR$^{o4}$);

each $A^{a3}$ to $A^{f3}$ independently represents a single bond, —N($R^{p4}$)— or —O—;

each $R^{a4}$ and $R^{f4}$ independently represents $C_{1-6}$ alkyl, $C_{2-6}$ alkenyl or $C_{2-6}$ alkynyl each optionally substituted by one or more groups independently selected from $G^{3a}$, or heterocyclyl optionally substituted by one or more groups independently selected from $G^{3b}$;

each $R^{b4}$, $R^{c4}$, $R^{d4}$, $R^{e4}$, $R^{g4}$, $R^{h4}$, $R^{i4}$, $R^{j4}$, $R^{k4}$, $R^{l4}$, $R^{m4}$, $R^{n4}$, $R^{o4}$ and $R^{p4}$ independently represents H, $C_{1-6}$ alkyl, $C_{2-6}$ alkenyl or $C_{2-6}$ alkynyl each optionally substituted by one or more groups independently selected from $G^{3a}$ or heterocyclyl optionally substituted by one or more groups independently selected from $G^{3b}$; or any of $R^{c4}$ and $R^{d4}$, $R^{g4}$ and $R^{h4}$ and/or $R^{j4}$ and $R^{k4}$ are linked together to form, together with the nitrogen atom to which they are attached, a 3- to 6-membered ring, which ring optionally contains one further heteroatom and which ring optionally is substituted by one or more groups independently selected $G^{3b}$;

each $G^{3a}$ and $G^{3b}$ independently represents halo, $R^{a5}$, —CN, —N($R^{b5}$)$R^{c5}$, —OR$^{d5}$, —SR$^{e5}$ or =O;

each $R^{a5}$ independently represents $C_{1-6}$ alkyl, $C_{2-6}$ alkenyl or $C_{2-6}$ alkynyl each optionally substituted by one or more groups independently selected from $G^4$;

each $R^{b5}$, $R^{c5}$, $R^{d5}$ and $R^{e5}$ independently represents H, $C_{1-6}$ alkyl, $C_{2-6}$ alkenyl or $C_{2-6}$ alkynyl each optionally substituted by one or more groups independently selected from $G^4$; or each $R^{b5}$ and $R^{c5}$ are linked together to form, together with the nitrogen atom to which they are attached, a 3- to 6-membered ring, which ring optionally contains one further heteroatom and which ring optionally is substituted by one or more groups independently selected from $G^4$;

each $G^4$ independently represents halo, $R^{a6}$, —CN, —N($R^{b6}$)$R^{c6}$, —OR$^{d6}$ or =O;

each $R^{a6}$ independently represents $C_{1-6}$ alkyl, $C_{2-6}$ alkenyl or $C_{2-6}$ alkynyl each optionally substituted by one or more fluoro;

each $R^{b6}$, $R^{c6}$ and $R^{d6}$ independently represents H, or $C_{1-6}$ alkyl, $C_{2-6}$ alkenyl or $C_{2-6}$ alkynyl each optionally substituted by one or more fluoro; and each p and q independently represents 1 or 2, which compounds and pharmaceutically acceptable salts thereof may be referred to as compounds of the invention, but with the provisos that the compound of formula I does not represent:

(A)
3-nitro-2-(piperidin-4-ylsulfonyl)pyridine, tert-butyl 3-((3-nitropyridin-2-yl)sulfonyl)pyrrolidine-1-carboxylate, tert-butyl (R)-3-((3-nitropyridin-2-yl)sulfonyl)pyrrolidine-1-carboxylate, tert-butyl (S)-3-((3-nitropyridin-2-yl)sulfonyl)pyrrolidine-1-carboxylate, tert-butyl 3-((3-nitropyridin-2-yl)sulfonyl)piperidine-1-carboxylate, or tert-butyl 4-((3-nitropyridin-2-yl)sulfonyl)piperidine-1-carboxylate;

or (B)
3-nitro-2-(4-piperidinylsulfinyl)-pyridine, 3-nitro-2-(3-pyrrolidinylsulfinyl)-pyridine, 3-nitro-2-(3-piperidinylsulfinyl)-pyridine, 4-[(3-nitro-2-pyridinyl)sulfinyl]-1-piperidinecarboxylic acid 1,1-dimethylethyl ester, 3-[(3-nitro-2-pyridinyl)sulfinyl]-1-pyrrolidinecarboxylic acid 1,1-dimethylethyl ester, 3-[(3-nitro-2-pyridinyl)sulfinyl]-1-piperidinecarboxylic acid 1,1-dimethylethyl ester, or 3-[(3-nitro-2-pyridinyl)sulfinyl]-7-oxabicyclo[2.2.1]hept-5-ene-2-carboxylic acid ethyl ester.

For the avoidance of doubt, compounds of formula I and pharmaceutically acceptable salts thereof, not including the provisos, may be referred to herein as compounds of the invention. Similarly, references to compounds of the first aspect of the invention will refer to compounds of formula I as defined in the first aspect of the invention, including the provisos, and pharmaceutically acceptable salts thereof. As such, compounds of the first aspect of the invention represent a particular embodiment of compounds of the invention.

The skilled person will understand that references herein to compounds of the invention (e.g. compounds of the first aspect of the invention) will include references to all embodiments and particular forms thereof.

Unless indicated otherwise, all technical and scientific terms used herein have the same meaning as commonly understood by one of ordinary skill in the art to which this invention pertains.

Pharmaceutically-acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline forms, such forms may include solvates, which are included in the scope of the invention. Compounds of the invention may also exist in solution.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution); for example, with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

As used herein, references to halo and/or halogen will independently refer to fluoro, chloro, bromo and iodo (for example, fluoro and chloro).

Unless otherwise specified, $C_{1-z}$ alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{3-z}$ partial cycloalkyl group). Part cyclic alkyl groups that may be mentioned include cyclopropylmethyl and cyclohexylethyl. When there is a sufficient number of carbon atoms, such groups may also be multicyclic (e.g. bicyclic or tricyclic) or spirocyclic.

Unless otherwise specified, $C_{2-z}$ alkenyl groups (where z is the upper limit of the range) defined herein may be straight-chain or, when there is a sufficient number (i.e. a minimum of three) of carbon atoms, be branched-chain, and/or cyclic (so forming a $C_{4-z}$ cycloalkenyl group). When there is a sufficient number (i.e. a minimum of five) of carbon atoms, such groups may also be part cyclic. Part cyclic alkenyl groups that may be mentioned include cyclopentenylmethyl and cyclohexenylmethyl. When there is a sufficient number of carbon atoms, such groups may also be multicyclic (e.g. bicyclic or tricyclic) or spirocyclic.

Unless otherwise specified, $C_{2-z}$ alkynyl groups (where z is the upper limit of the range) defined herein may be straight-chain or, when there is a sufficient number (i.e. a minimum of four) of carbon atoms, be branched-chain.

For the avoidance of doubt, the skilled person will understand that the term alkyl will refer to saturated hydrocarbon moieties, whereas the term alkenyl will refer to unsaturated hydrocarbon moieties containing at least one carbon-carbon double bond and the term alkynyl will refer to unsaturated hydrocarbon moieties containing at least one carbon-carbon triple bond, which alkyl, alkenyl and alkynyl groups may be referred to collectively as hydrocarbyl groups. Further, such unsaturated hydrocarbon moieties will be referred to by reference to the highest degree of unsaturation comprised therein (e.g. a hydrocarbon moiety comprising at least one carbon-carbon double bond and at least one carbon-carbon triple bond will be referred to as alkynyl, although such moieties may also be referred to using terms such as "alkenyl alkynyl" and the like).

As used herein, the term heterocyclyl may refer to non-aromatic monocyclic and bicyclic heterocyclyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocyclyl group). Further, such heterocyclyl groups may be saturated, forming a heterocycloalkyl, or unsaturated containing one or more carbon-carbon or, where possible, carbon-heteroatom or heteroatom-heteroatom double and/or triple bonds, forming for example a $C_{2-z}$ (e.g. $C_{4-z}$) heterocycloalkenyl (where z is the upper limit of the range) or a $C_{7-z}$ heterocycloalkynyl group. $C_{2-z}$ heterocyclyl groups that may be mentioned include 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, 2,3-dihydroisothiazolyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, tetrahydrothiopyranyl, thiomorpholinyl, trithianyl (including 1,3,5-trithianyl), tropanyl and the like. Substituents on heterocyclyl groups may, where appropriate, be located on any atom in the ring system including a heteroatom. Further, in the case where the substituent is another cyclic compound, then the cyclic compound may be attached through a single atom on the heterocyclyl group, forming a so-called "spiro"-compound. The point of attachment of heterocyclyl groups may be via any atom in the ring system including (where appropriate) a further heteroatom (such as a nitrogen atom), or an atom on any fused carbocyclic ring that may be present as part of the ring system. Heterocyclyl groups may also be in the N- or S-oxidised form.

At each occurrence when mentioned herein, particular heterocyclyl groups that may be mentioned include 3- to 8-membered heterocyclyl groups (e.g. a 4- to 6-membered heterocyclyl group).

As may be used herein, the term aryl includes references to $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like, such as phenyl). For the avoidance of doubt, the point of attachment of substituents on aryl groups may be via any carbon atom of the ring system.

As may be used herein, the term heteroaryl (or heteroaromatic) includes references to 5- to 14-(e.g. 5- to 10-) membered heteroaromatic groups containing one or more heteroatoms selected from oxygen, nitrogen and/or sulfur. Such heteroaryl groups may comprise one, two, or three rings, of which at least one is aromatic. Substituents on heteroaryl/heteroaromatic groups may, where appropriate, be located on any atom in the ring system including a heteroatom. The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocyclyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl. The oxides of heteroaryl/heteroaromatic groups are also embraced within the scope of the invention (e.g. the N-oxide). As stated above, heteroaryl includes polycyclic (e.g. bicyclic) groups in which one ring is aromatic (and the other may or may not be aromatic). Hence, other heteroaryl groups that may be mentioned include e.g. benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, 1,2,3,4-tetrahydroquinolinyl, thiochromanyl and the like.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulfur (e.g. oxygen, nitrogen and sulfur).

For the avoidance of doubt, references to polycyclic (e.g. bicyclic) groups (e.g. when employed in the context of heterocyclyl groups) will refer to ring systems wherein more than two scissions would be required to convert such rings into a straight chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of heterocyclyl groups) may refer to groups in which the second ring of a two-ring system is formed between two adjacent atoms of the first ring, and may also refer to groups in which two non-adjacent atoms are linked by either an alkylene or heteroalkylene chain (as appropriate), which later groups may be referred to as bridged.

For the avoidance of doubt, when an aryl or an heteroaryl group is substituted with a group via a double bond, such as =O, it is understood that the aryl or heteroaryl group is partly aromatic, i.e. the aryl or heteroaryl group consists of at least two rings where at least one ring is not aromatic.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more Y groups are present, those Y groups may be the same or different. Similarly, where two or more Y groups are present and each represent $R^{a1}$, the $R^{a3}$ groups in question may be the same or different. Likewise, when more than one $R^{a1}$ is present and each independently represents $C_{1-6}$ alkyl substituted by one or more $G^{1a}$ group, the identities of each $G^{1a}$ are in no way interdependent.

For the avoidance of doubt, when a term such as "$A^{a1}$ to $A^{f1}$" is employed herein, this will be understood by the skilled person to mean $A^{a1}$, $A^{b1}$, $A^{c1}$, $A^{d1}$, $A^{e1}$ and $A^{f1}$ inclusively.

Unless otherwise stated, the same reasoning will apply to other such terms used herein.

The skilled person will appreciate that compounds of the invention that are the subject of this invention include those that are stable. That is, compounds of the invention include those that are sufficiently robust to survive isolation, e.g. from a reaction mixture, to a useful degree of purity.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

Particular compounds of the invention that may be mentioned include those in which n represents 2.

Further compounds of the invention that may be mentioned include those in which n represents 1.

Particular compounds of the invention that may be mentioned include those in which X represents saturated heterocyclyl, which may be referred to as heterocycloalkyl.

More particular compounds of the invention include those in which X represents 3- to 7-membered heterocyclyl (e.g. heterocycloalkyl).

Yet more particular compounds of the invention include those in which X represents 5- or 6-membered heterocyclyl (e.g. heterocycloalkyl).

Yet more particular compounds of the invention include those in which X represents 5- or 6-membered heterocyclyl (e.g. heterocycloalkyl) comprising (i.e. containing as a constituent member of the ring) one heteroatom, particularly wherein the one heteroatom is selected from O and N (e.g. wherein, when the heteroatom is N, that N atom is substituted with Y).

Particular compounds of the invention that may be mentioned include those in which X represents saturated heterocyclyl (which may be referred to as heterocycloalkyl).

Particular compounds of formula I that may be mentioned include those in which X represents unsubstituted tetrahydrofuranyl (e.g. tetrahydrofuran-3-yl), tetrahydro-2H-pyranyl (e.g. tetrahydro-2H-pyran-4-yl) or piperidinyl (e.g. piperidin-4-yl), optionally substituted by one or more (e.g. one) Y group.

More particular compounds of the invention that may be mentioned include those in which X represents unsubstituted tetrahydropyranyl (e.g. tetrahydropyran-4-yl).

Yet more particular compounds of formula I that may be mentioned include those in which X represents tetrahydrofuranyl (e.g. tetrahydrofuran-3-yl) or piperidinyl (e.g. piperidin-4-yl), optionally substituted by one or more (e.g. one) Y group.

Particular compounds of the invention that may be mentioned include those in which:

X represents heterocyclyl substituted by one or more groups independently selected from Y;

each Y independently represents halo, $R^{a3}$, —CN, -$A^{a2}$-$C(Q^{a2})R^{b3}$, -$A^{b2}$-$C(Q^{b2})N(R^{c3})R^{d3}$, -$A^{c2}$-$C(Q^{c2})OR^{e3}$, -$A^{d2}$-$S(O)_qR^{f3}$, -$A^{e2}$-$S(O)_qN(R^{g3})R^{h3}$, -$A^{f2}$-$S(O)_qOR^{i3}$, —$N(R^{j3})R^{k3}$, —$OR^{l3}$, —$SR^{m3}$ or =O;

each $Q^{a2}$ to $Q^{e2}$ independently represents =O, =S, =$NR^{n3}$ or =$N(OR^{o3})$;

each $A^{a2}$ to $A^{e2}$ independently represents a single bond, —$N(R^{p3})$— or —O—;

each $R^{a3}$ and $R^{f2}$ independently represents $C_{1-6}$ alkyl, $C_{2-6}$ alkenyl or $C_{2-6}$ alkynyl (e.g. $C_{1-6}$ alkyl) each optionally substituted by one or more groups independently selected from $G^{2a}$, heterocyclyl optionally substituted by one or more groups independently selected from $G^{2b}$, aryl optionally substituted by one or more groups independently selected from $G^{2c}$, or heteroaryl optionally substituted by one or more groups independently selected from $G^{2d}$;

each $R^{b3}$, $R^{c3}$, $R^{d3}$, $R^{e3}$, $R^{g3}$, $R^{h3}$, $R^{i3}$, $R^{k3}$, $R^{l3}$, $R^{m3}$, $R^{n3}$, $R^{o3}$ and $R^{p3}$ independently represents H, $C_{1-6}$ alkyl, $C_{2-6}$ alkenyl or $C_{2-6}$ alkynyl (e.g. $C_{1-6}$ alkyl) each optionally substituted by one or more groups independently selected from $G^{2a}$, heterocyclyl optionally substituted by one or more groups independently selected from $G^{2b}$, aryl optionally substituted by one or more groups independently selected from $G^{2c}$, or heteroaryl optionally substituted by one or more groups independently selected from $G^{2d}$, or any two $R^{c3}$ and $R^{d3}$, $R^{g3}$ and $R^{h4}$ and/or $R^{j3}$ and $R^{k3}$ are linked together to form, along with the nitrogen atom to which they are attached, a 3- to 6-membered ring, which ring optionally contains one further heteroatom and which ring optionally is substituted by one or more groups independently selected from heterocyclyl optionally substituted by one or more groups independently selected from $G^{2b}$, aryl optionally substituted by one or more groups independently selected from $G^{2c}$, or heteroaryl optionally substituted by one or more groups independently selected from $G^{2d}$, and =O;

each $G^{2a}$ independently represents halo, —CN, —$N(R^{j4})R^{k4}$, —$OR^{l4}$, —$SR^{m4}$ or =O;

each $G^{2b}$ independently represents halo, $R^{a4}$, —CN, —$N(R^{j4})R^{k4}$, —$OR^{l4}$, —$SR^{m4}$ or =O;

each $G^{2c}$ and $G^{2d}$ independently represents halo, $R^{a4}$, —CN, -$A^{a3}$-$C(Q^{a3})R^{b4}$, -$A^{b3}$-$C(Q^{b3})N(R^{c4})R^{d4}$, -$A^{c3}$-$C(Q^{c4})OR^{e4}$, -$A^{d3}$-$S(O)_qR^{f4}$, -$A^{e3}$-$S(O)_qN(R^{g4})R^{h4}$, -$A^{f3}$-$S(O)_qOR^{i4}$, —$N_3$, —$N(R^{j4})R^{k4}$, —N(H)CN, —$NO_2$, —$ONO_2$, —$OR^{l4}$ or —$SR^{m4}$;

each $Q^{a3}$ to $Q^{c3}$ independently represents =O, =S, =$NR^{n4}$ or =$N(OR^{o4})$;

each $A^{a3}$ to $A^{f3}$ independently represents a single bond, —$N(R^{p4})$— or —O—;

each $R^{a1}$ and $R^{f3}$ independently represents $C_{1-6}$ alkyl, $C_{2-6}$ alkenyl or $C_{2-6}$ alkynyl (e.g. $C_{1-6}$ alkyl) each optionally substituted by one or more groups independently selected from $G^{3a}$, or heterocyclyl optionally substituted by one or more groups independently selected from $G^{3b}$;

each $R^{b4}$, $R^{c4}$, $R^{d4}$, $R^{e4}$, $R^{g4}$, $R^{h4}$, $R^{i4}$, $R^{j4}$, $R^{k4}$, $R^{l4}$, $R^{m4}$, $R^{n4}$, $R^{o4}$ and $R^{p4}$ independently represents H, $C_{1-6}$ alkyl, $C_{2-6}$ alkenyl or $C_{2-6}$ alkynyl (e.g. $C_{1-6}$ alkyl) each optionally substituted by one or more groups independently selected from $G^{3a}$ or heterocyclyl optionally substituted by one or more groups independently selected from $G^{3b}$, or any of $R^{c4}$ and $R^{d4}$, $R^{g4}$ and $R^{h4}$ and/or $R^{j4}$ and $R^{k4}$ are linked together to form, together with the nitrogen atom to which they are attached, a 3- to 6-membered ring, which ring optionally contains one further heteroatom and which ring optionally is substituted by one or more groups independently selected $G^{3b}$;

each $G^{3a}$ and $G^{3b}$ independently represents halo, $R^{a5}$, —CN, —$N(R^{b5})R^{c5}$, —$OR^{d5}$, —$SR^{e5}$ or =O; each $R^{a5}$ independently represents $C_{1-6}$ alkyl, $C_{2-6}$ alkenyl or $C_{2-6}$ alkynyl (e.g. $C_{1-6}$ alkyl) each optionally substituted by one or more groups independently selected from $G^4$;

each $R^{b5}$, $R^{c5}$, $R^{d5}$ and $R^{e5}$ independently represents H, or $C_{1-6}$ alkyl, $C_{2-6}$ alkenyl or $C_{2-6}$ alkynyl (e.g. $C_{1-6}$ alkyl) each optionally substituted by one or more groups independently selected from $G^4$, or each $R^{b5}$ and $R^{c5}$ are linked together to form, together with the nitrogen atom to which they are attached, a 3- to 6-membered ring, which ring optionally contains one further heteroatom and which ring optionally is substituted by one or more groups independently selected $G^4$;

each $G^4$ independently represents halo, $R^{a6}$, —CN, —$N(R^{b6})R^{c6}$, —$OR^{d6}$ or =O;

each $R^{a6}$ independently represents $C_{1-6}$ alkyl, $C_{2-6}$ alkenyl or $C_{2-6}$ alkynyl (e.g. $C_{1-6}$ alkyl) each optionally substituted by one or more fluoro;

each $R^{b6}$, $R^{c6}$ and $R^{d6}$ independently represents H, or $C_{1-6}$ alkyl, $C_{2-6}$ alkenyl or $C_{2-6}$ alkynyl (e.g. $C_{1-6}$ alkyl) each optionally substituted by one or more fluoro; and/or (e.g. and)

each p and q independently represents 1 or 2.

Particular compounds of the invention that may be mentioned include those in which each Y independently represents halo (e.g. fluoro) fluoro, $R^{a3}$, —N(H)—$C(O)R^{b3}$, —$C(O)OR^{e3}$, —N(H)—$S(O)_2R^2$, —$S(O)_2R^2$, —N(H)—$S(O)_qN(R^{g3})R^{h3}$, —$N(R^{j3})R^{k3}$ or —$OR^{l3}$.

More particular compounds of the invention that may be mentioned include those in which each Y independently represents halo (e.g. fluoro), $R^{a3}$, —$C(O)OR^{e3}$, —$N(R^{j3})R^{k3}$ or Yet more particular compounds of the invention that may be mentioned include those in which each Y independently represents halo (e.g. fluoro) fluoro, $R^{a3}$ or —$C(O)OR^{e3}$ (such as $R^{a3}$ or —$C(O)OR^{e3}$), particular in which $R^{a3}$ and/or (e.g. and) —$R^{e3}$ represent $C_{1-3}$ alkyl (e.g. methyl) optionally substituted with one or more fluoro (such as —$CH_3$).

For example, compounds of the invention that may be mentioned include those in which each Y independently represents methyl or —$C(O)CH_3$.

More particular compounds of the invention that may be mentioned include those in which:

X represents heterocyclyl (e.g. $C_{2-7}$ heterocyclyl, such as $C_{2-7}$ heterocycloalkyl) substituted by one or more (e.g. one) groups independently selected from Y;

each Y independently represents fluoro, $R^{a3}$, —N(H)—C(O)$R^{b3}$, —C(O)O$R^{e3}$, —N(H)—S(O)$_2R^{f3}$, —S(O)$_2R^2$, —N(H)—S(O)$_qN(R^{g3})R^{h3}$, —N($R^{j3}$)$R^{k3}$ or —O$R^{l3}$; and/or (e.g. and) each $R^{b3}$, $R^{e3}$, $R^{f3}$, $R^{g3}$, $R^{h3}$, $R^{e3}$, $R^{j3}$, $R^{k3}$ and $R^{l3}$ independently represents H, or $C_{1-3}$ alkyl, $C_{2-3}$ alkenyl or $C_{2-3}$ alkynyl (e.g. $C_{1-3}$ alkyl), or any two $R^{g3}$ and $R^{h3}$ and/or $R^{j3}$ and $R^{k3}$ are linked together to form, together with the nitrogen atom to which they are attached, a 3- to 6-membered ring, which ring optionally contains one further nitrogen and which ring optionally is substituted by one or more $C_{1-3}$ alkyl, $C_{2-3}$ alkenyl or $C_{2-3}$ alkynyl (e.g. $C_{1-3}$ alkyl).

Yet more particular compounds of the invention that may be mentioned include those in which:

X represents $C_{2-6}$ heterocyclyl (e.g. $C_{2-6}$ heterocyclyl, such as $C_{2-6}$ heterocycloalkyl) substituted by one or more groups (e.g. one group) independently selected from Y;

each Y independently represents halo (e.g. fluoro), $R^{a3}$, —C(O)O$R^{e3}$, —N($R^{j3}$)$R^{k3}$ or —O$R^{l3}$;

each $R^{a3}$, $R^{e3}$, $R^{j3}$, $R^{k3}$ and $R^{l3}$ independently represents H or $C_{1-3}$ alkyl (e.g. —CH$_3$), or $R^{j3}$ and $R^{k3}$ are linked together to form, together with the nitrogen atom to which they are attached, a 3- to 6-membered ring (e.g a 5- to 6-membered ring), which ring optionally contains one further nitrogen and which ring optionally is substituted by one or more (e.g. one) $C_{1-3}$ alkyl (e.g. —CH$_3$).

Particular compounds of the invention that may be mentioned include those in which each $R^1$, $R^2$ and $R^3$ each independently represents H, halo (e.g. fluoro or chloro, such as chloro), $R^{a1}$, —N($R^{j1}$)$R^{k1}$ or —O$R^{l1}$.

More particular compounds of the invention that may be mentioned include those in which:

each $R^{a1}$ and $R^{l1}$ independently represents $C_{1-6}$ alkyl, $C_{2-6}$ alkenyl or $C_{2-6}$ alkynyl each optionally substituted by one or more groups independently selected from $G^{1a}$, or heterocyclyl optionally substituted by one or more groups independently selected from $G^{1b}$; and each $R^{b1}$, $R^{c1}$, $R^{d1}$, $R^{e1}$, $R^{g1}$, $R^{h1}$, $R^{i1}$, $R^{j1}$, $R^{k1}$, $R^{l1}$, $R^{m1}$, $R^{n1}$, $R^{o1}$ and $R^{p1}$ independently represents H, $C_{1-6}$ alkyl, $C_{2-6}$ alkenyl or $C_{2-6}$ alkynyl each optionally substituted by one or more groups independently selected from $G^{1a}$ or heterocyclyl optionally substituted by one or more groups independently selected from $G^{1b}$; or any of $R^{c1}$ and $R^{d1}$, $R^{g1}$ and $R^{h1}$ and/or $R^{j1}$ and $R^{k1}$ are linked together to form, together with the nitrogen atom to which they are attached, a 3- to 6-membered ring, which ring optionally contains one further heteroatom and which ring optionally is substituted by one or more groups independently selected from halo, and $C_{1-3}$ alkyl, $C_{2-3}$ alkenyl or $C_{2-3}$ alkynyl each optionally substituted by one or more halo, and =O.

More particular compounds of the invention that may be mentioned include those in which: each $R^1$, $R^2$ and $R^3$ independently represents H, halo (e.g. fluoro or chloro), $R^{a1}$, —N($R^{j1}$)$R^{k1}$, —O$R^{l1}$ or —S$R^{m1}$ (e.g. H, halo, such as chloro or fluoro, $R^{a1}$, —N($R^{j1}$)$R^{k1}$ or —O$R^{l1}$); and/or (e.g. and)

each $R^{a1}$, $R^{j1}$, $R^{k1}$, $R^{l1}$ and $R^{m1}$ independently represent $C_{1-6}$ alkyl, $C_{2-6}$ alkenyl or $C_{1-6}$ alkynyl (e.g. $C_{1-6}$ alkyl, such as methyl) optionally substituted by one or more fluoro (e.g. —CH$_3$).

In particular embodiments that may be mentioned, only $R^{c1}$ and $R^{d1}$, and/or $R^{g1}$ and $R^{h1}$ may alternatively be linked together in the manner described herein.

For example, compounds of the invention that may be mentioned include those in which:

each $R^1$, $R^2$ and $R^3$ each independently represent H or —O$R^{l1}$; and each $R^{l1}$ independently represents $C_{1-6}$ alkyl, $C_{2-6}$ alkenyl, $C_{2-6}$ alkynyl each optionally substituted by one or more fluoro (such as methyl, difluoromethyl, trifluoromethyl), or —N($R^{a2}$)$R^{b2}$, or heterocyclyl optionally substituted by one $G^{1b}$;

each $R^{a2}$ and $R^{b2}$ independently represents H or $C_{1-6}$ alkyl, $C_{2-6}$ alkenyl, $C_{2-6}$ alkynyl (e.g. $C_{1-6}$ alkyl, such as methyl), or $R^{a2}$ and $R^{b2}$ are linked together to form, along with the nitrogen atom to which they are attached, a 3- to 6-membered ring, which ring optionally contains one further heteroatom and which ring optionally is substituted by one or more groups independently selected from $C_{1-3}$ alkyl; and/or (e.g. and)

$G^{1b}$ represents $C_{1-3}$ alkyl and =O.

Further compounds of the invention that may be mentioned include those in which each $R^1$, $R^2$ and $R^3$ independently represents H, halo (e.g. chloro), —N($R^{j1}$)$R^{k1}$ or —O$R^{l1}$.

In particular, compounds of the invention may be mentioned include those in which:

each $R^1$, $R^2$ and $R^3$ each independently represent H, halo (e.g. chloro), —N($R^{j1}$)$R^{k1}$ or —O$R^{l1}$;

each $R^{l1}$ independently represents $C_{1-6}$ alkyl, $C_{2-6}$ alkenyl or $C_{2-6}$ alkynyl each optionally substituted by one or more fluoro (such as methyl, difluoromethyl, trifluoromethyl), or —N($R^{a2}$)$R^{b2}$, or heterocyclyl optionally substituted by one $G^{1b}$; and/or (e.g. and)

each $R^{j1}$ and $R^{k1}$ independently represent $C_{1-6}$ alkyl, $C_{2-6}$ alkenyl or $C_{2-6}$ alkynyl (e.g. $C_{1-6}$ alkyl, such as methyl) each optionally substituted by one or more fluoro (e.g. —CH$_3$).

Yet more particular compounds the invention that may be mentioned include those in which:

each $R^1$, $R^2$ and $R^3$ each independently represent H or —O$R^{l1}$; and/or (e.g. and)

each $R^{l1}$ independently represents $C_{1-6}$ alkyl (e.g. $C_{1-3}$ alkyl, such as methyl) optionally substituted by one or more fluoro (e.g. —CH$_3$).

Particular compounds of the invention that may be mentioned include those in which each of $R^1$, $R^2$ and $R^3$ represent H.

Particular compounds of the invention that may be mentioned include those in which at least one (e.g. one) of $R^1$, $R^2$ and $R^3$ (e.g. $R^1$) represents a group other than H and the remainder of $R^1$, $R^2$ and $R^3$ represent H, particularly where the group other than H is:

—O$R^{l1}$ (such as —O$R^{l1}$ where $R^{l1}$ represents $C_{1-6}$ alkyl (e.g. $C_{1-6}$ alkyl, such as methyl) optionally substituted by one or more fluoro);

halo, such as chloro; or

—N($R^{j1}$)$R^{k1}$, such as —NMe$_2$.

For example, compounds of the invention that may be mentioned include those in which at least one (e.g. one) of $R^1$, $R^2$ and $R^3$ (e.g. $R^1$) represents —O$C_{1-6}$ alkyl optionally substituted by one or more fluoro (e.g. —OCH$_3$), halo (e.g. chloro) or —N($R^{j1}$)$R^{k1}$ (e.g. —NMe$_2$), and the remainder of $R^1$, $R^2$ and $R^3$ represent H.

Thus, in a particular embodiment, there is provided a compound of the invention where:

$R^2$ and $R^3$ represent H; and/or (e.g. and)

$R^1$ represents H or, particularly, halo (e.g. fluoro or chloro, such as chloro), $R^{a1}$, —N($R^{j1}$)$R^{k1}$, —O$R^{l1}$ or —S$R^{m1}$ (e.g. H, halo, such as chloro, $R^{a1}$, —N($R^{j1}$)$R^{k1}$ or —O$R^{l1}$).

In a more particular embodiment, there is provided a compounds of the invention where:

$R^2$ and $R^3$ represent H; and/or (e.g. and)

$R^1$ represents H or, particularly, halo, $R^{a1}$, —N($R^{j1}$)$R^{k1}$, —O$R^{j1}$ or —S$R^{m1}$ (e.g. H, halo, $R^{a1}$, —N($R^{j1}$)$R^{k1}$ or —O$R^{j1}$), wherein each $R^{a1}$, $R^{j1}$, $R^{k1}$, $R^{l1}$ and $R^{m1}$ independently represent $C_{1-6}$ alkyl (e.g. $C_{1-3}$ alkyl, such as methyl) optionally substituted by one or more fluoro (e.g. —CH$_3$).

In a yet more particular embodiment, there is provided a compound of the invention wherein:

$R^2$ and $R^3$ represent H; and/or (e.g. and)

$R^1$ represents H or —O$C_{1-6}$ alkyl (e.g. —O$C_{1-3}$ alkyl) optionally substituted by one or more fluoro (e.g. —OCH$_3$).

For example, there are provided compounds of the invention wherein:

$R^2$ and $R^3$ represent H; and/or (e.g. and)

$R^1$ represents —OCH$_3$.

Thus, particular of the compounds of the invention of the invention that may be mentioned include those in which $R^1$ represents —OCH$_3$.

As indicated herein above, particular features and embodiments as described herein may be combined without departing from the teaching of the invention.

For example, in a particular embodiment of the invention, there is provided a compound of formula I wherein:

X represents unsubstituted heterocyclyl (e.g. $C_{2-8}$ heterocyclyl); and each $R^1$, $R^2$ and $R^3$ each independently represents H, halo, $R^{a1}$, —N($R^{j1}$)$R^{k1}$ or —O$R^{j1}$.

Particular compounds of the invention (including compounds of formula I and all embodiments and particular forms thereof) that may be mentioned include the compounds of the examples as provided herein, or a pharmaceutically acceptable salt thereof.

Where an example compound is indicated to have been obtained in a particular salt form, the skilled person will understand that particular compounds of the invention that may be mentioned include the free base or free acid (as appropriate) of that compound, and vice versa. Further, where an example compound is indicated to have been obtained in a particular salt form, particular compounds of the invention that may be mentioned include other (i.e. different) pharmaceutically acceptable salts of that compound.

Thus, for the avoidance of doubt, particular compounds of the invention that may be mentioned include:
6-methoxy-2-((2-methyltetrahydrofuran-3-yl)sulfonyl)-3-nitropyridine,
6-methoxy-2-((1-methylpiperidin-4-yl)sulfonyl)-3-nitropyridine,
1-(4-((6-methoxy-3-nitropyridin-2-yl)sulfonyl)piperidin-1-yl)ethan-1-one, and
6-methoxy-3-nitro-2-((tetrahydro-2H-pyran-4-yl)sulfonyl)pyridine
and pharmaceutically acceptable salts thereof.

Compositions and Medical Uses

As discussed hereinbefore, compounds of the invention, and therefore compositions and kits comprising the same, are useful as pharmaceuticals.

According to a second aspect of the invention there is provided a compound of the invention, as hereinbefore defined (i.e. in the first aspect of the invention, including all embodiments and particular features therein, but without the provisos), for use as a pharmaceutical. Further, there is provided a compound of the invention, as hereinbefore defined, for use in medicine.

In a particular embodiment of the second aspect of the invention, the compound of the invention is a compound of the first aspect of the invention (i.e. including the provisos).

As indicated herein, compounds of the invention may be of particular use in treating cancers.

Thus, in a third aspect of the invention, there is provided a compound of the invention, as hereinbefore defined (i.e. in the first aspect of the invention, including all embodiments and particular features therein, but without the provisos), for use in the treatment of cancer.

In an alternative third aspect of the invention, there is provided the use of a compound of the invention, as hereinbefore defined, in the manufacture of a medicament for the treatment of cancer.

In a further alternative third aspect of the invention, there is provided a method of treating cancer comprising administering to a patient in need thereof a therapeutically effective amount of a compound of the invention.

In a particular embodiment of the third aspect of the invention, the compound of the invention is a compound of the first aspect of the invention (i.e. including the provisos).

The skilled person will understand that references to the treatment of a particular condition (or, similarly, to treating that condition) take their normal meanings in the field of medicine.

In particular, the terms may refer to achieving a reduction in the severity of one or more clinical symptom associated with the condition. For example, in the case of a cancer, the term may refer to achieving a reduction of the amount of cancerous cells present (e.g. in the case of a cancer forming a solid tumour, indicated by a reduction in tumour volume).

As used herein, references to patients will refer to a living subject being treated, including mammalian (e.g. human) patients.

As used herein, the term effective amount will refer to an amount of a compound that confers a therapeutic effect on the treated patient. The effect may be objective (i.e.

measurable by some test or marker) or subjective (i.e. the subject gives an indication of and/or feels an effect).

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the active compounds of the invention to which they are metabolised), may also be described as "prodrugs".

Thus, the compounds of the invention are useful because they possess pharmacological activity, and/or are metabolised in the body following oral or parenteral administration to form compounds that possess pharmacological activity.

Without wishing to be bound by theory, it is believed that compounds of the invention wherein n represents 1 may be metabolised in vivo to form corresponding compounds of the invention wherein n represents 2.

As indicated herein, the compounds of the invention may be useful in the treatment of cancer (i.e. particular cancers).

Particular cancers that may be mentioned include those selected from the group comprising:

soft tissue cancers, such as sarcoma (e.g. angiosarcoma, fibrosarcoma, rhabdomyosarcoma, liposarcoma), myxoma, rhabdomyoma, fibroma, lipoma and teratoma;

lung cancers, such as bronchogenic carcinoma (e.g. squamous cell, undifferentiated small cell, undifferentiated large cell, adenocarcinoma), alveolar (or bronchiolar) carcinoma, bronchial adenoma, sarcoma, lymphoma, chondromatous hamartoma, mesothelioma, including non-small cell lung cancer;

gastrointestinal cancers: such as esophageal cancers (e.g. squamous cell carcinoma, adenocarcinoma, leiomyosarcoma, lymphoma), stomach cancers (e.g. carcinoma, lymphoma, leiomyosarcoma), pancreatic cancers (e.g. ductal adenocarcinoma, insulinoma, glucagonoma, gastrinoma, carcinoid tumors, vipoma), small bowel cancers (e.g. adenocarcinoma, lymphoma, carcinoid tumors, Kaposi's sarcoma, leiomyoma, hemangioma, lipoma, neurofibroma, fibroma), large bowel cancers (e.g. adenocarcinoma, tubular adenoma, villous adenoma, hamartoma, leiomyoma);

genitourinary tract cancers, such as cancer of the kidney (e.g. adenocarcinoma, Wilm's tumor (nephroblastoma), lymphoma, leukemia), bladder and urethra (e.g. squamous cell carcinoma, transitional cell carcinoma, adenocarcinoma), prostate (e.g. adenocarcinoma, sarcoma), testis (e.g. seminoma, teratoma, embryonal carcinoma, teratocarcinoma, choriocarcinoma, sarcoma, interstitial cell carcinoma, fibroma, fibroadenoma, adenomatoid tumors, lipoma);

liver cancers, such as hepatoma (e.g. hepatocellular carcinoma), cholangiocarcinoma, hepatoblastoma, angiosarcoma, hepatocellular adenoma, hemangioma;

bone cancers, such as osteogenic sarcoma (e.g. osteosarcoma), fibrosarcoma, malignant fibrous histiocytoma, chondrosarcoma, Ewing's sarcoma, malignant lymphoma (e.g. reticulum cell sarcoma), multiple myeloma, malignant giant cell tumor chordoma, osteochronfroma (e.g osteocartilaginous exostoses), benign chondroma, chondroblastoma, chondromyxofibroma, osteoid osteoma and giant cell tumors;

cancers of the head and/or nervous system, such as cancer of the skull (e.g. osteoma, hemangioma, granuloma, xanthoma, osteitis deformans), meninges (e.g. meningioma, meningiosarcoma, gliomatosis), brain (e.g. astrocytoma, medulloblastoma, glioma, ependymoma, germinoma (pinealoma), glioblastoma multiform, oligodendroglioma, schwannoma, retinoblastoma, congenital tumors), spinal cord (e.g. neurofibroma, meningioma, glioma, sarcoma);

gynecological cancers, such as cancers of the uterus (e.g. endometrial carcinoma), cervix (cervical carcinoma, pretumor cervical dysplasia), ovaries (e.g. ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), cancers of the vulva (e.g. squamous cell carcinoma, intraepithelial carcinoma, adenocarcinoma, fibrosarcoma, melanoma), vagina (e.g. clear cell carcinoma, squamous cell carcinoma, botryoid sarcoma (embryonal rhabdomyosarcoma)), fallopian tubes (e.g. carcinoma);

haematologic cancers, such as cancers of the blood and bone marrow (e.g. myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma);

skin cancers, such as malignant melanoma, basal cell carcinoma, squamous cell carcinoma, Kaposi's sarcoma, moles dysplastic nevi, lipoma, angioma, dermatofibroma, keloids; neurofibromatosis and Adrenal glands; and neuroblastomas.

As used herein, references to cancerous cells and the like will include references to a cell afflicted by any one of the above identified conditions.

More particular cancers that may be mentioned include those corresponding to the cell lines used in the examples provided herein.

For example, particular cancers that may be mentioned include breast cancer (such as mammary adenocarcinoma, e.g. metastatic mammary adenocarcinoma) and/or glioblastoma (such as glioblastoma multiform).

More particular cancers that may be mentioned include:

head and neck cancer (such as throat cancer, e.g. pharyngeal squamous cell carcinoma);

colon cancer (such as colorectal carcinoma);

skin cancer (such as epidermoid (skin) carcinoma);

gastrointestinal cancers (such as pancreatic cancer, e.g. pancreatic ductal carcinoma);

breast cancer (such as mammary adenocarcinoma, e.g. metastatic mammary adenocarcinoma);

lung cancer (such as carcinoma); and haematologic cancers (such as leukemia, e.g. acute monocytic leukemia).

In particular embodiments, the cancer is a solid tumor cancer.

In more particular embodiments, the cancer is selected from pancreatic cancer, ovarian cancer and colorectal cancer.

For example, in certain embodiments, the cancer is selected from colorectal cancer (including those processing Ras mutations), small cell lung cancer, non-small cell lung cancer (NSCLC), and glioma.

In other embodiments, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer.

In further embodiments, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma.

In certain embodiments of the present invention, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostate cancer The skilled person will understand that treatment with compounds of the invention may further comprise (i.e. be combined with) further treatment(s) for the same condition. In particular, treatment with compounds of the invention may be combined with means for the treatment of cancer, such as treatment with one or more other therapeutic agent that is useful in the in the treatment of cancer and/or one or more physical method used in the treatment of cancer (such as treatment through surgery), as known to those skilled in the art.

In particular, treatment with compounds of the invention may be performed in patients who are being or have been (i.e. as part or of a treatment for the same condition, such as within a month of treatment with compounds of the invention, such as within two weeks, e.g. within a week or, particularly, on the same day) treated with a therapeutic agent or physical method that is capable of causing (e.g. can be demonstrated to cause) an increase in reactive oxygen species.

For the avoidance of doubt, the skilled person will understand that therapeutic agents or physical methods capable of causing (e.g. can be demonstrated to cause) an increase in reactive oxygen species may not necessarily be effective treatments per se, but will become effective when used in combination with compounds of the invention.

For the avoidance of doubt, the skilled person will understand that compounds of the invention may also be used in combination with one or more other therapeutic agent that is useful in the in the treatment of cancer and/or one or more physical method used in the treatment of cancer (such as treatment through surgery) wherein such methods do not cause an increase in reactive oxygen species.

In particular, treatment with compounds of the invention may be performed in patients who are being or have been treated with radiotherapy.

Thus, there is also provided:

a method of treating cancer in a patient in need thereof wherein the patient is administered a therapeutically effective amount of a compound of the invention in combination with treatment by radiotherapy (i.e. concomitantly or sequentially); and a compound of the invention for use in treating cancer in a patient who is also being treated with radiotherapy.

Compounds of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Compounds of the invention may be administered alone or may be administered by way of known pharmaceutical compositions/formulations, including tablets, capsules or elixirs for oral administration, suppositories for rectal administration, sterile solutions or suspensions for parenteral or intramuscular administration, and the like.

According to a fourth aspect of the invention there is thus provided a pharmaceutical composition/formulation comprising a compound of the invention as hereinbefore defined (i.e. in the first aspect of the invention, including all embodiments and particular features therein, but without the provisos), and optionally (e.g. in admixture with) one or more pharmaceutically acceptable adjuvant, diluent and/or carrier.

In a particular embodiment of the fourth aspect of the invention, the compound of the invention is a compound of the first aspect of the invention (i.e. including the provisos).

The skilled person will understand that references herein to compounds of the invention being for particular uses (and, similarly, to uses and methods of use relating to compounds of the invention) may also apply to pharmaceutical compositions comprising compounds of the invention as described herein.

Compounds of the invention may be administered in the form of tablets or capsules, e.g. time-release capsules that are taken orally. Alternatively, the compounds of the invention may be in a liquid form and may be taken orally or by injection. The compounds of the invention may also be in the form of suppositories, or, creams, gels, and foams e.g. that can be applied to the skin. In addition, they may be in the form of an inhalant that is applied nasally or via the lungs.

The skilled person will understand that compounds of the invention may act systemically and/or locally (i.e. at a particular site).

Compounds of the invention may be administered orally, intravenously, subcutaneously, buccally, rectally, dermally, nasally, tracheally, bronchially, by any other parenteral route or via inhalation, in a pharmaceutically acceptable dosage form. Alternatively, particularly where compounds of the invention are intended to act locally, compounds of the invention may be administered topically.

Thus, in a particular embodiment, the pharmaceutical formulation is provided in a pharmaceutically acceptable dosage form, including tablets or capsules, liquid forms to be taken orally or by injection, suppositories, creams, gels, foams, or inhalants (e.g. to be applied intranasally). For the avoidance of doubt, in such embodiments, compounds of the invention may be present as a solid (e.g. a solid dispersion), liquid (e.g. in solution) or in other forms, such as in the form of micelles.

In more particular embodiments, the pharmaceutical formulation is provided the form of a tablets or capsules, liquid forms to be taken orally or by injection (e.g. a form suitable for intravenous injection). In particular, injection may take place using conventional means, and may include the use of microneedles.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

As described herein, compounds of the invention may also be combined with one or more other (i.e. different, e.g. agents other than compounds of formula I) therapeutic agents that are useful in the treatment of cancer. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a fifth aspect of the invention, there is provided a combination product comprising:

(A) a compound of the invention as hereinbefore defined (i.e. in the first aspect of the invention, including all embodiments and particular features therein, but without the provisos); and (B) one or more other therapeutic agent that is useful in the treatment of cancer, wherein each of components (A) and (B) is formulated in admixture, optionally with one or more a pharmaceutically-acceptable adjuvant, diluent or carrier.

In a sixth aspect of the invention there is provided a kit-of-parts comprising:

(a) a pharmaceutical formulation as hereinbefore defined (i.e. in the fourth aspect of the invention); and (b) one or more other therapeutic agent that is useful in the treatment of cancer, optionally in admixture with one or more pharmaceutically-acceptable adjuvant, diluent or carrier, which components (a) and (b) are each provided in a form that is suitable for administration in conjunction (i.e. concomitantly or sequentially) with the other.

In particular embodiments of the fourth and fifth aspects of the invention, the compound of the invention is a compound of the first aspect of the invention (i.e. including the provisos).

The skilled person will understand that compounds of the invention, and pharmaceutically-acceptable salts thereof, may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 0.01 µg/kg of body weight per day (µg/kg/day) to about 200 µg/kg/day, preferably about 0.01 to about 10 µg/kg/day, and more preferably about 0.1 to about 5.0 µg/kg/day. For example, when administered orally, treatment with such compounds may comprise administration of a formulations typically containing between about 0.01 µg to about 2000 mg, for example between about 0.1 µg to about 500 mg, or between 1 µg to about 100 mg (e.g. about 20 µg to about 80 mg), of the active ingredient(s). When administered intravenously, the most preferred doses will range from about 0.001 to about 10 µg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 10 mg, 20 mg, 30 mg or 40 mg twice daily).

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

In further aspects of the invention, there is provided a process for the preparation of a combination product or kit-of-parts as hereinbefore defined, which process comprises bringing into association a compound of the invention, as hereinbefore defined, or a pharmaceutically acceptable salt thereof with the other therapeutic agent that is useful in the treatment of cancer, and at least one pharmaceutically-acceptable adjuvant, diluent or carrier.

As used herein, references to bringing into association will mean that the two components are rendered suitable for administration in conjunction with each other.

Thus, in relation to the process for the preparation of a kit of parts as hereinbefore defined, by bringing the two components "into association with" each other, we include that the two components of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Compounds of the invention as described herein may be prepared in accordance with techniques that are well known to those skilled in the art, such as those described in the examples provided hereinafter.

According to a seventh aspect of the invention there is provided a process for the preparation of a compound of the first aspect of the invention as hereinbefore defined (i.e. a compound of the invention but including the provisos), which process comprises:

(i) where n represents 2, reaction of a compound of formula IIA

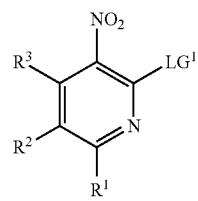

(IIA)

wherein $R^1$, $R^2$ and $R^3$ are as defined herein (i.e. for compounds of the invention, or any particular feature or embodiment thereof) and $LG^1$ represents a suitable leaving group (such as halo, e.g. chloro), with a compound of formula IIIA

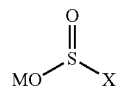

(IIIA)

wherein X is as defined herein (i.e. for compounds of the invention, or any particular feature or embodiments thereof) and M represents an alkali metal ion (such as a Na ion), in the presence of a suitable acid (such as a concentrated acid, e.g. a concentrated mineral acid, for example concentrated HCl, e.g. concentrated aqueous HCl) and in the presence of a suitable solvent (such as a polar organic solvent, e.g. N,N'-dimethylacetamide, N,N'-dimethylformamide or tetrahydrofuran), and optionally in the presence of a suitable phase transfer catalyst (such as a quaternary ammonium salt, e.g. tetra-butyl ammonium chloride);

(ii) where n represents 2, reaction of a compound of formula IIB

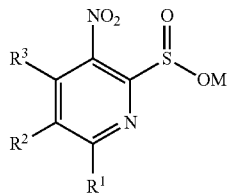

wherein $R^1$, $R^2$ and $R^3$ are as defined herein (i.e. for compounds of the invention, or any particular feature or embodiments thereof) and M represents an alkali metal ion (such as a Na ion), with a compound of formula IIIB

wherein X is as defined herein in formula I (i.e. for compounds of the invention, or any particular feature or embodiments thereof) and $LG^2$ represents a suitable leaving group (such as halo, e.g. chloro), in the presence of a suitable acid (such as a concentrated acid, e.g. a concentrated mineral acid, for example concentrated HCl, e.g. concentrated aqueous HCl) and in the presence of a suitable solvent (such as a polar organic solvent, e.g. N,N'-dimethylacetamide, N,N'-dimethylformamide or tetrahydrofuran), and optionally in the presence of a suitable phase transfer catalyst (such as a quaternary ammonium salt, e.g. tetra-butyl ammonium chloride);

(iii) where n represents 2, reaction of a compound of formula IIA as hereinbefore defined with a compound of formula IIIA as hereinbefore defined, in the presence of a suitable metal halide (such as a suitable metal iodide, e.g. CuI, or a suitable metal bromide, e.g. CuBr; which metal halide may be present in excess, such as in amount corresponding to at least 2 molar equivalents of the compound of formula IIA and/or the compound of formula IIIA) and in the presence of a suitable solvent (such as a polar organic solvent, e.g. N,N'-dimethylacetamide, N,N'-dimethylformamide, tetrahydrofuran or 3-dimethyl-2-imidazolidinone), under conditions known to those skilled in the art;

(iv) where n represents 2, reaction of a compound of formula IIB as hereinbefore defined with a compound of formula IIIB as hereinbefore defined, in the presence of a suitable metal halide (such as a suitable metal iodide, e.g. CuI, or a suitable metal bromide, e.g. CuBr; which metal halide may be present in excess, such as in amount corresponding to at least 2 molar equivalents of the compound of formula IIB and/or the compound of formula IIIB) and in the presence of a suitable solvent (such as a polar organic solvent, e.g. N,N'-dimethylacetamide, N,N'-dimethylformamide, tetrahydrofuran or 3-dimethyl-2-imidazolidinone), under conditions known to those skilled in the art;

(v) reaction of a compound of formula IV

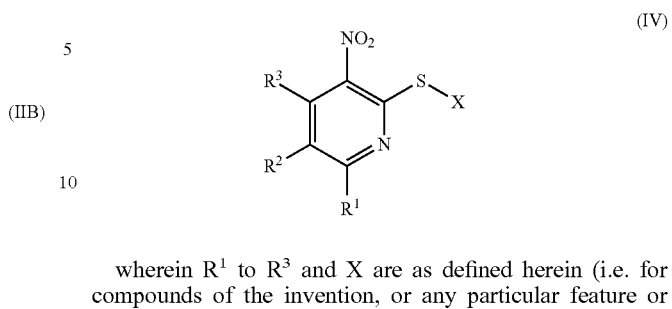

wherein $R^1$ to $R^3$ and X are as defined herein (i.e. for compounds of the invention, or any particular feature or embodiments thereof), with a suitable oxidising agent (i.e. an oxidising agent chosen and used in a manner as required to achieved the desired degree of oxidation; such as a hypochlorite salt, e.g. sodium hypochlorite, a peroxymonosulfate salt, e.g. potassium peroxymonosulfate (Oxone), a percarboxylic acid, e.g. meta-chloroperoxybenzoic acid (mCPBA), or potassium permanganate) in the presence of a suitable solvent (such as a polar organic solvent, e.g. N,N'-dimethylacetamide, N,N'-dimethylformamide or tetrahydrofuran), and optionally in the presence of water, under conditions known to those skilled in the art;

(vi) where n represents 2, reaction of a compound of formula V

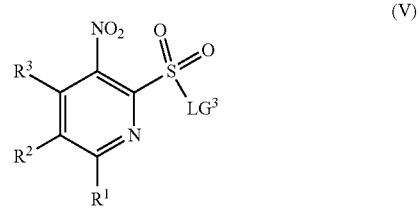

wherein $R^1$, $R^2$ and $R^3$ are as defined herein (i.e. for compounds of the invention, or any particular feature or embodiments thereof) and $LG^3$ represents a suitable leaving group (such as halo, e.g. chloro) with a compound of formula VI

wherein X is as defined (i.e. for compounds of the invention, or any particular feature or embodiments thereof), in the presence of a suitable Lewis acid (such as $AlCl_3$) and in the presence of a suitable solvent (such as an organic solvent, e.g. dichloromethane or dichloroethane).

Compounds of formulae IIA, IIB, IIIA, IIIB, IV, V and VI are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, 3$^{rd}$ edition, published by Chapman & Hall, "*Comprehensive Heterocyclic Chemistry II*" by A. R. Katritzky, C. W. Rees and E. F. V. Scriven, Pergamon Press, 1996 and "*Science of*

Synthesis", Volumes 9-17 (Hetarenes and Related Ring Systems), Georg Thieme Verlag, 2006.

In particular, compounds of formula IV may be prepared by reaction of a compound of formula VII

wherein X is as defined herein (i.e. for compounds of the invention, or any particular feature or embodiments thereof), with a compound of formula IIA as herein before defined, under conditions known to those skilled in the art, such as in the presence of a suitable base (such as a metal carbonate, e.g. potassium carbonate, a metal hydroxide, e.g. sodium hydroxide, or an amine base, e.g. triethyl amine), and in the presence of a suitable solvent (such as a polar organic solvent, e.g. N,N'-dimethylacetamide, N,N'-dimethylformamide or tetrahydrofuran, or a mixture of a polar organic solvent and water), under conditions known to those skilled in the art.

Similarly, compounds of formula IV may be prepared by reaction of a compound of formula VII

wherein X is as defined herein (i.e. for compounds of the invention, or any particular feature or embodiments thereof), with a compound of formula IIA as herein before defined, under conditions known to those skilled in the art, such as in the presence of a suitable base (such as a metal carbonate, e.g. potassium carbonate, a metal hydroxide, e.g. sodium hydroxide, or an amine base, e.g. triethyl amine), and in the presence of a suitable solvent (such as a polar organic solvent, e.g. N,N'-dimethylacetamide, N,N'-dimethylformamide or tetrahydrofuran, or a mixture of a polar organic solvent and water), under conditions known to those skilled in the art.

Similarly, compounds of formula IV (particularly where at least one Y is present and represents an electron-withdrawing group, such as —$NO_2$) may be prepared by reaction of a compound of formula IX

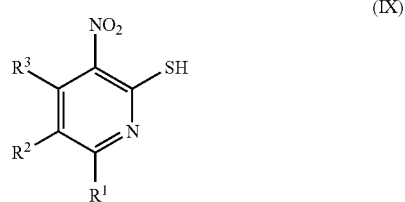

wherein $R^1$, $R^2$ and $R^3$ are as defined herein (i.e. for compounds of the invention, or any particular feature or embodiments thereof), with a compound of formula III B as described herein, under conditions known to those skilled in the art (for example, where the $R^4$ groups present in the compound of formula IIIB are not sufficiently electron withdrawing, the reaction may be performed in the presence of a suitable catalyst, such as palladium(II) acetate or copper oxide, in which case the suitable base may be an alkali metal tert-butoxide, such as Kt-OBu).

Similarly, compounds of formulae VIII and IX are either commercially available, are known in the literature, or may be obtained either by analogy with the processes described herein, or by conventional synthetic procedures, in accordance with standard techniques, from available starting materials using appropriate reagents and reaction conditions.

The substituents $R^1$ to $R^3$ and Y, as hereinbefore defined, may be modified one or more times, after or during the processes described above for preparation of compounds of formula I by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention (e.g. isolation and optionally purification of the compound of formula I).

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999).

In a further aspect of the invention, there is provided a compound of formula IV as defined herein (i.e. wherein $R^1$, $R^2$, $R^3$ and X are as defined herein, including all particular features and embodiments thereof), or a pharmaceutically acceptable salt thereof.

Particular compounds of formula IV that may be mentioned include those prepared in the examples provided herein, and pharmaceutically acceptable salts thereof.

Compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

Without wishing to be bound by theory, it is thought that inhibition of thioredoxin reductase is obtained by the utilization of strong electrophilicity of small molecule inhibitors in combination with a pronounced inherent nucleophilicity of NADPH-reduced, but not oxidized, thioredoxin reductase, resulting in selective and potent inhibition of said enzyme without major targeting of other cellular pathways or enzymes.

Moreover, it is thought that normal non-cancerous cells may survive without a functional cytosolic thioredoxin reductase enzyme because of maintained function of the glutathione system, while cancer cells cannot survive upon specific inhibition of cytosolic thioredoxin reductase.

EXAMPLES

The invention is illustrated by way of the following examples, in which the following abbreviations may be employed.
aq aqueous
BSA bovine serum albumin
conc concentrated
DMA N,N'-dimethylacetamide
DMF N,N'-dimethylformamide
DMSO dimethyl sulfoxide
DTNB 5,5'-dithio-bis-(2-nitrobenzoic acid)
EDTA ethylenediaminetetraacetic add
GSSG glutathione disulfide
HPLC high performance liquid chromatography
HRMS high resolution mass spectrometry
mCPBA meta-chloroperbenzoic acid
NADPH nicotinamide adenine dinucleotide phosphate
NMR nuclear magnetic resonance
PBS phosphate buffered saline
rt room temperature Starting materials and chemical reagents specified in the syntheses described below are commercially available from a number of suppliers, such as Sigma Aldrich.

In the event that there is a discrepancy between nomenclature and the structure of compounds as depicted graphically, it is the latter that presides (unless contradicted by any experimental details that may be given and/or unless it is clear from the context). The names of the final compounds may be translated to the structures e.g. using ChemBioDraw Ultra 14.

Example 1: 6-Methoxy-2-(((2-methyltetrahydrofuran-3-yl)sulfonyl)-3-nitropyridine

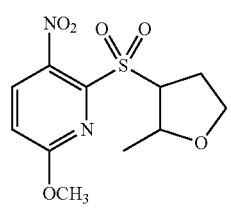

(a) 6-Methoxy-2-((2-methyltetrahydrofuran-3-yl)thio)-3-nitropyridine

A mixture of 2-chloro-6-methoxy-3-nitropyridine (250 mg, 1.33 mmol), 2-methyl-tetrahydrofuran-3-thiol (172 mg, 1.46 mmol), $K_2CO_3$ (220 mg, 1.59 mmol) and DMF (5 mL) was stirred at rt overnight. Water was added and the mixture extracted with EtOAc. The combined extracts were washed with $H_2O$, brine and dried over $Na_2SO_4$. Concentration and purification by chromatography gave the sub-title compound (99 mg, 29%).

(b) 6-Methoxy-2-((2-methyltetrahydrofuran-3-yl)sulfonyl)-3-nitropyridine mCPBA (224 mg, 1.28 mmol) was added to a stirred mixture of 6-methoxy-2-((2-methyl-tetrahydrofuran-3-yl)thio)-3-nitropyridine (99 mg, 0.37 mmol) and $CH_2Cl_2$ (10 mL) at rt. The mixture was stirred at rt overnight, diluted with $CH_2Cl_2$ (10 mL) and washed with aq $Na_2S_2O_3$ (aq, sat) and brine, and dried over $Na_2SO_4$. Purification by chromatography gave the title compound (21 mg, 19%).

The following compounds where obtained using the procedure above.

| Ex | Chemical structure<br>Name<br>$^1$H-NMR [solvent, δ] | MS [m/z (M + H)$^+$] |
|---|---|---|
| 2 | ![structure] <br> 1-(4-((6-methoxy-3-nitropyridin-2-yl)sulfonyl)piperidin-1-yl)ethan-1-one $^1$H-NMR [CDCl$_3$, δ 8.08 (d, J = 8.56 Hz, 1H), 7.07 (d, J = 8.76 Hz, 1H), 4.75-4.71(m, 1H), 4.07 (s, 3H), 4.01-3.99 (m, 2H), 3.19-3.16 (m, 1H), 2.68-2.65 (m, 1H), 2.21-2.17 (m, 1H), 2.11 (s, 3H), 2.02-1.88 (m, 3H)] | MS [m/z (M + H)$^+$ = (Calculated for $C_{13}H_{17}N_3O_6S$ + H: 344.09) found: 343.6] |
| 3 | ![structure] <br> 6-methoxy-3-nitro-2-((tetrahydro-2H-pyran-4-yl)sulfonyl)pyridine $^1$H-NMR [DMSO-d$_6$ δ 8.48 (d, J = 9 Hz, 1H), 7.39 (d, J = 9 Hz, 1H), 4.26-4.20 (m, 1H), 4.02 (s, 3H), 3.97-3.94 (m, 2H), 3.45-3.39 (m, 2H), 1.88-1.84 (m, 2H), 1.74-1.68 (m, 2H)] | MS [m/z (M + H)$^+$ = (Calculated for $C_{11}H_{14}N_2O_6S$ + H: 303.07) found: 303.1] |

Example 4: 6-Methoxy-2-(2-methyl-tetrahydrofuran-3-ylsulfinyl)-3-nitro-pyridine

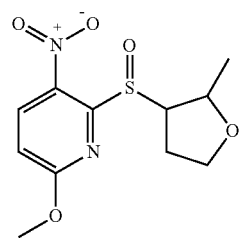

(a) 6-Methoxy-2-(2-methyl-tetrahydro-furan-3-ylsulfanyl)-3-nitro-pyridine

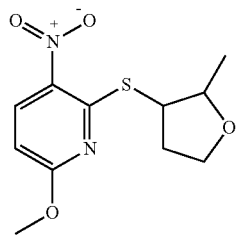

To a solution of 6-methoxy-2-chloro-3-nitro pyridine (1 g, 5.319 mmol) in dimethylformamide (5 mL) was added potassium carbonate (880 mg, 6.382 mmol) and 2-methyloxolane-3-thiol (690 mg, 5.851 mmol) at room temperature. The reaction mixture was stirred for 12 hours at room temperature. Progress of reaction was monitored by LCMS. The reaction mixture was quenched with ice cold water (20 mL) and was extracted with ethyl acetate (50 mL). The organic layer was washed with water (3×30 mL) followed by brine (1×50 mL). The organic layer was dried over anhydrous sodium sulphate and was evaporated under reduced pressure to give the crude product which was purified by column chromatography eluting with 7% ethyl acetate in hexane affording the sub-title compound as yellow solid (700 mg, 48%).

$^1$H NMR (DMSO-$d_6$, 400 MHz) δ 8.51-8.48 (m, 1H), 6.79-6.76 (m, 1H), 4.56-3.85 (m, 6H), 3.78-3.63 (m, 1H), 2.71-2.62 (m, 1H), 1.98-1.92 (m, 1H), 1.28-1.14 (m, 3H);

$^{13}$C NMR (DMSO-$d_6$, 100 MHz) δ 164.2, 164.1, 157.5, 157.5, 137.4, 136.0, 107.0, 106.9, 78.1, 78.1 75.8, 65.9, 65.1, 54.9, 54.8, 47.7, 45.9, 33.6, 32.2, 19.5, 16.8;

LCMS [m/z (M+H)$^+$] 271 (MW calc=270); Diastereomeric mixture $R_t$=2.42, 2.45; HPLC purity at λ=210 nm: Diastereomeric mixture $R_t$=8.84, 22.98%; $R_t$=8.81, 75.37%.

(b) 6-Methoxy-2-(2-methyl-tetrahydro-furan-3-ylsulfinyl)-3-nitro-pyridine

To a solution of 6-methoxy-2-(2-methyl-tetrahydro-furan-3-ylsulfanyl)-3-nitro-pyridine (450 mg, 1.666 mmol) in dichloromethane (10 mL) was added m-chloro per benzoic acid (343.86 mg, 1.999 mmol) at 0° C. The reaction mixture was stirred at the same temperature for 3 hours. Progress of reaction was monitored by LCMS. The reaction mixture was quenched with sodium sulphite and sodium bicarbonate (1:1) solution for 20 minutes. The reaction mixture was extracted with dichloromethane (3×20 mL) and combined organic layer was washed with brine (1×20 mL). The organic layer was separated and dried over anhydrous sodium sulphate and was evaporated under reduced pressure to give the crude product which was purified by column chromatography eluting with 2% methanol in dichloromethane affording the title compound as yellow solid (190 mg, 40%).

$^1$H NMR (DMSO-$d_6$, 400 MHz) δ 8.59-8.54 (m), 7.21-7.13 (m), 4.53-3.38 (m), 4.09 (s), 2.8-2.6 (m), 2.49-2.25 (m), 1.75-1.58 (m), 1.61 (d, J=6.4 Hz), 1.49 (d, J=6.5 Hz), 1.40 (d, J=6.1 Hz), 0.76 (d, J=6.3 Hz);

$^{13}$C NMR (DMSO-$d_6$, 100 MHz) δ 165.7, 165.6, 165.6, 161.5, 160.4, 159.6, 137.6, 137.1, 137.0, 136.8, 136.7, 113.8, 112.9, 112.5, 112.3, 76.3, 70.34, 67.2, 66.3, 66.3, 65.8, 65.6, 65.4, 64.1, 63.5, 55.2, 55.15, 30.37, 26.45, 21.7, 21.0, 20.1, 18.8, 16.6; LCMS [m/z (M+H)$^+$] 287 (MW calc=286); Diastereomeric mixture $R_t$=7.29, 7.59, 7.71, 8.02;

HPLC purity at A=210 nm: Diastereomeric mixture $R_t$=8.54, 7.4%; $R_t$=8.84, 56.8%; $R_t$=8.95, 16.3%; $R_t$=9.25, 18.4%

Example 5: 6-Methoxy-3-nitro-2-(tetrahydro-pyran-4-ylsulfinyl)-pyridine

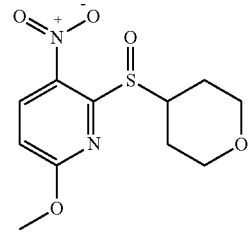

(a) 6-Methoxy-3-nitro-2-(tetrahydro-pyran-4-ylsulfanyl)-pyridine

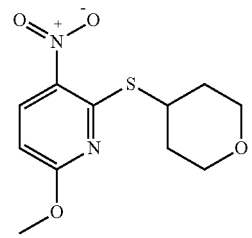

To a solution of 6-methoxy-2-chloro-3-nitro pyridine (1 g, 5.319 mmol) in dimethylformamide (5 mL) was added potassium carbonate (880 mg, 6.382 mmol) and oxane-4-thiol (690 mg, 5.851 mmol) at room temperature. The reaction mixture was stirred for 12 hours at room temperature. Progress of reaction was monitored by LCMS. The reaction mixture was quenched with ice cold water (20 mL) and was extracted with ethyl acetate (50 mL). The organic layer was washed with water (3×30 mL) followed by brine (1×50 mL). The organic layer was dried over anhydrous sodium sulphate and was evaporated under reduced pressure to give the crude product which was purified by column chromatography eluting with 10% ethyl acetate in hexane affording the sub-title compound as an off white solid (1.2 g, 83.5%).

$^1$H NMR (DMSO-$d_6$, 400 MHz) δ 8.48 (d, J=9.0 Hz, 1H), 6.75 (d, J=9.0 Hz, 1H), 4.21-4.11 (m, 1H), 4.02 (s, 3H), 3.91-3.86 (m, 2H), 3.53-3.47 (m, 2H), 2.05-2.02 (m, 2H), 1.70-1.65 (m, 2H);

$^{13}$C NMR (DMSO-$d_6$, 100 MHz) δ 164.0, 157.0, 137.3, 135.5, 106.7, 66.6 (2C), 54.6, 39.4, 32.0 (2C);

LCMS [m/z (M+H)$^+$] 271 (MW calc=270); $R_t$=1.66

(b) 6-Methoxy-3-nitro-2-(tetrahydro-pyran-4-ylsulfinyl)-pyridine

To a solution of 6-methoxy-3-nitro-2-(tetrahydro-pyran-4-ylsulfanyl)-pyridine (800 mg, 2.962 mmol) in dichloromethane (10 mL) was added m-chloro per benzoic acid (611.55 mg, 3.555 mmol) at 0° C. The reaction mixture was stirred at room temperature for 4 hours. Progress of reaction was monitored by LCMS. The reaction mixture was quenched with sodium sulphite and sodium bicarbonate (1:1) solution for 20 minutes. The reaction mixture was extracted with dichloromethane (3×20 mL) and combined organic layer was washed with brine (1×20 mL). The organic layer was separated and dried over anhydrous sodium sulphate and was evaporated under reduced pressure to give the crude product which was purified by column chromatography eluting with 1.5% methanol in dichloromethane affording the title compound as a light yellow solid (270 mg, 32%).

$^1$H NMR (DMSO-$d_6$, 400 MHz) δ 8.57 (d, J=8.96 Hz, 1H), 7.16 (d, J=8.96 Hz, 1H), 4.07 (s, 3H), 3.96-3.86 (m, 2H), 3.51-3.25 (m, 3H), 1.91-1.81 (m, 3H), 1.25-1.18 (m, 1H);

$^{13}$C NMR (CDCl$_3$, 100 MHz) δ 166.3, 160.4, 137.7, 136.0, 112.9, 67.0, 66.6, 58.6, 55.7, 28.0, 23.1;

LCMS [m/z (M+H)$^+$] 287 (MW calc=286); R$_t$=1.32
HPLC purity at A=220 nm: 99.53%.

Example 6: 1-[4-(6-Methoxy-3-nitro-pyridin-2-ylsulfinyl)-piperidin-1-yl]-ethanone

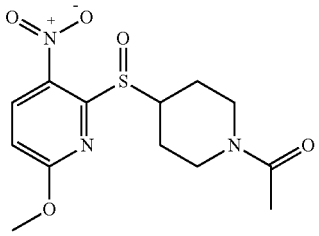

(a) 1-[4-(6-Methoxy-3-nitro-pyridin-2-ylsulfanyl)-piperidin-1-yl]-ethanone

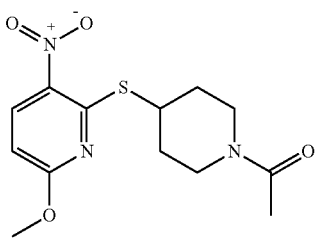

To a solution of 6-methoxy-2-chloro-3-nitro pyridine (1 g, 5.319 mmol) in dimethylformamide (5 mL) was added potassium carbonate (880 mg, 6.382 mmol) and 1-(4-sulfanylpiperidin-1-yl) ethan-1-one (930 mg, 5.851 mmol) at room temperature. The reaction mixture was stirred for 12 hours at room temperature. Progress of reaction was monitored by LCMS. The reaction mixture was filtered. The filtrate was evaporated under reduced pressure to give the crude product which was purified by column chromatography eluting with 2% methanol in dichloromethane and triturated with ether to afford the sub-title compound as yellow solid (1.2 g, 72.5%).

$^1$H NMR (DMSO-$d_6$, 400 MHz) δ 8.49 (d, J=9.1 Hz, 1H), 6.77 (d, J=9.1 Hz, 1H), 4.27-4.24 (m, 1H), 4.16-4.09 (m, 1H), 4.03 (s, 3H), 3.84-3.80 (m, 1H), 3.27-3.23 (m, 1H), 2.92-2.86 (m, 1H), 2.13-2.07 (m, 2H), 2.01 (s, 3H), 1.69-1.59 (m, 1H), 1.54-1.50 (m, 1H);

$^{13}$C NMR (DMSO-$d_6$, 100 MHz) δ 167.9, 164.1, 156.9, 137.4, 135.5, 106.7, 54.7, 45.5, 40.6, 40.4, 31.6, 31.0, 21.2;

LCMS [m/z (M+H)$^+$] 312 (MW calc=311); R$_t$=1.57

(b) 1-[4-(6-Methoxy-3-nitro-pyridin-2-ylsulfinyl)-piperidin-1-yl]-ethanone

To a solution of 1-[4-(6-methoxy-3-nitro-pyridin-2-ylsulfanyl)-piperidin-1-yl]-ethanone (850 mg, 2.733 mmol) in dichloromethane (10 mL) was added m-chloro per benzoic acid (564 mg, 3.279 mmol) at 0° C. The reaction mixture was stirred at the same temperature for 3 hours. Progress of reaction was monitored by LCMS. The reaction mixture was quenched with sodium sulphite and sodium bicarbonate (1:1) solution for 20 minutes. The reaction mixture was extracted with dichloromethane (3×20 mL) and combined organic layer was washed with brine (1×20 mL). The organic layer was separated and dried over anhydrous sodium sulphate and was evaporated under reduced pressure to give the crude product which was purified by column chromatography eluting with 4% methanol in dichloromethane to afford the title compound, (250 mg, 28%) as yellow solid.

$^1$H NMR (DMSO-$d_6$, 400 MHz) δ 8.60-8.57 (m, 1H), 7.18-7.15 (m, 1H), 4.5-4.4 (m, 1H), 4.07 (s, 3H), 3.95-3.85 (m, 1H), 3.55-3.45 (m, 1H), 3.15-2.95 (m, 1H), 2.65-2.53 (m, 1H), 2.11-1.95 (m, 4H), 1.85-1.55 (m, 2H), 1.39-1.33 (m, 1H);

$^{13}$C NMR (DMSO-$d_6$, 100 MHz) δ 167.9, 165.4, 159.8, 159.7 137.8, 137.13, 137.09, 112.5, 57.47, 57.35, 55.22, 55.21, 45.0, 44.4, 40.2, 39.5, 27.9, 27.2, 22.4, 21.5, 21.12, 21.08; MS [m/z (M+H)$^+$] 328 (MW calc=327); R$_t$=1.85;

HPLC purity at o=200 nm: 97.72%.

BIOLOGICAL EXAMPLES

Biological Example 1: Inhibition of Recombinant TrxR1 and GR

Small molecule inhibition of recombinant thioredoxin reductase 1 (TrxR1) and gluthathione reductase (GR) was examined in 96-well plate format. 30 nM TrxR1 was incubated in the presence of 250 μM NADPH, 0.1 mg/ml BSA, and various concentrations of compound (1% DMSO final) in 50 mM Tris (pH 7.5) and 2 mM EDTA buffer for 15 minutes. Following the incubation period, 2 mM DTNB was added to each well and the change in O.D. at 412 nm was followed. Percent activity was determined using DMSO vehicle and no TrxR1 (blank) controls. 2 nM GR was incubated in the presence of 250 μM NADPH, 0.1 mg/ml BSA, and various concentrations of compounds (1% DMSO final) in 50 mM Tris (pH 7.5) and 2 mM EDTA buffer for 15 minutes. Following the incubation period, 1 mM GSSG was added to each well and the change in O.D. at 340 nm was followed. Percent activity was determined using DMSO vehicle and no GR (blank) controls.

Using the assays described in Biological Example 1, the following IC$_{50}$ values were obtained. The results obtained are provided in Table 1 below.

33

| Example # | TrxR Assay IC50 (nM) | GR Assay IC50 (μM) |
| --- | --- | --- |
| 1 | 93.0 | >100 μM |
| 2 | 391 | >100 μM |
| 3 | 39.06 | >100 μM |
| 4 | 1010 | >100 μM |
| 5 | 4330 | >100 μM |
| 6 | 4060 | >100 μM |

Biological Example 2: Breast Cancer Cell Viability Assay

MDA-MB-231 cells were plated 2000 cells/well in 96-well black optical plates in the presence of 10% FBS media containing 25 nM selenite. The following day cells were treated with various concentrations of compounds (0.1% DMSO final) and incubated for 72 hrs. After the incubation Alamar Blue reagent was added to each well and incubated for additional 3 hrs. Fluorescence was read ex:530 nm/em:590 nm, and percent of viability was determined using DMSO vehicle and no cell (blank) controls.

Using the assays described in Biological Example 2, the following $IC_{50}$ values were obtained. The results obtained are provided in Table 2 below.

| Example # | MDA-MB-231 Cell viability IC50 (μM) |
| --- | --- |
| 1 | 4.53 |
| 2 | 12.29 |
| 3 | 5.08 |

Biological Example 3: Cancer Cell Viability Assay

Breast cancer and glioblastoma cell lines were plated 4000 cells/well in 96-well plates in the presence of 10% FBS media. The following day cells were treated with various concentrations of example compounds (0.1% DMSO final) and incubated for 72 hrs. After the incubation An MTT assay was performed to access cell viability. Percent of viability was determined using DMSO vehicle and no cell (blank) controls.

Using the assays described in Biological Example 3, the following $IC_{50}$ values were obtained. The results obtained are provided in Table 3 below.

| Example # | U-87 MG IC50 (μM) | MDA-MB-231 IC50 (μM) | MDA-MB-468 IC50 (μM) |
| --- | --- | --- | --- |
| 1 | 8.89 | 8.94 | 4.14 |
| 2 | 10.59 | 9.97 | 4 |
| 3 | 6.11 | 7.53 | 4.34 |
| 4 | 9.27 | 3.54 | 2.10 |
| 5 | — | 3.57 | 2.40 |
| 6 | — | 11.56 | 5.58 |

34

The invention claimed is:
1. A compound of formula I

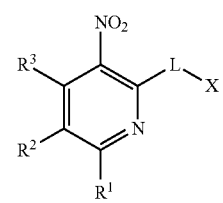

or a pharmaceutically acceptable salt thereof, wherein:
L represents —S(O)$_n$—;
n represents 2 or 1;
X represents a 5- or 6-membered non-aromatic heterocyclyl, connected to L via a carbon atom, and optionally substituted by one or more groups independently selected from Y;
$R^1$, $R^2$ and $R^3$ each independently represent H, halo, $R^{a1}$, —CN, C(O)$R^{b1}$, —C(S)$R^{b1}$, —C(N$R^{n1}$)$R^{b1}$, —C(N(O$R^{o1}$))$R^{b1}$, —N($R^{P1}$)—C(S)$R^{b1}$, N($R^{P1}$)—C(N$R^{n1}$)$R^{b1}$, —N($R^{P1}$)—C(N(O$R^{o1}$))$R^{b1}$, —O—C(O)$R^{b1}$, —O—C(S)$R^{b1}$, —O—C(N$R^{n1}$)$R^{b1}$, —O—C(N(O$R^{o1}$))$R^{b1}$, —C(O)N($R^{c1}$)$R^{d1}$, —C(S)N($R^{c1}$)$R^{d1}$, —C(N$R^{n1}$)N($R^{c1}$)$R^{d1}$, —C(N(O$R^{o1}$))N($R^{c1}$)$R^{d1}$, —N($R^{P1}$)—C(O)N($R^{c1}$)$R^{d1}$, —N($R^{P1}$)—C(S)N($R^{c1}$)$R^{d1}$, —N($R^{P1}$)—C(N$R^{n1}$)N($R^{c1}$)$R^{d1}$, —N($R^{P1}$)—C(N(O$R^{o1}$))N($R^{c1}$)$R^{d1}$, —O—C(O)N($R^{c1}$)$R^{d1}$, —O—C(S)N($R^{c1}$)$R^{d1}$, —O—C(N$R^{n1}$)N($R^{c1}$)$R^{d1}$, —O—C(N(O$R^{o1}$))N($R^{c1}$)$R^{d1}$, —C(O)O$R^{e1}$, —C(S)O$R^{e1}$, —C(N$R^{n1}$)O$R^{e1}$, —C(N(O$R^{o1}$))O$R^{e1}$, —N($R^{P1}$)—C(O)O$R^{e1}$, —N($R^{P1}$)—C(S)O$R^{e1}$, —N($R^{P1}$)—C(N$R^{n1}$)O$R^{e1}$, —N($R^{P1}$)—C(N(O$R^{o1}$))O$R^{e1}$, —O—C(O)O$R^{e1}$, —O—C(S)O$R^{e1}$, —O—C(N$R^{n1}$)O$R^{e1}$, —O—C(N(O$R^{o1}$))O$R^{e1}$, —S(O)$_p$$R^{f1}$, —N($R^{P1}$)—S(O)$_p$$R^{f1}$, —O—S(O)$_p$$R^{f1}$, —S(O)$_p$N($R^{g1}$)$R^{h1}$, —N($R^{P1}$)—S(O)$_p$N($R^{g1}$)$R^{h1}$, —O—S(O)$_p$N($R^{g1}$)$R^{hl}$, —S(O)$_p$O$R^{i1}$, —N($R^{P1}$)—S(O)$_p$O$R^{i1}$, —O—S(O)$_p$O$R^{i1}$, —N$_3$, —N($R^{j1}$)$R^{k1}$, —N(H)CN, —NO$_2$, —ONO$_2$, —O$R^{i1}$ or —S$R^{ml}$;
each $R^{a1}$ and $R^{f1}$ independently represents $C_{1-6}$ alkyl, $C_{2-6}$ alkenyl or $C_{2-6}$ alkynyl each optionally substituted by one or more groups independently selected from halo, —CN, —N($R^{a2}$)$R^{b2}$, —O$R^{c2}$, —S$R^{d2}$ and =O;
each $R^{b1}$, $R^{c1}$, $R^{d1}$, $R^{e1}$, $R^{f1}$, $R^{g1}$, $R^{h1}$, $R^{i1}$, $R^{j1}$, $R^{k1}$, $R^{l1}$, $R^{m1}$, $R^{n1}$, $R^{o1}$, $R^{b1}$, independently represents H or $C_1$-6 alkyl, $C_2$-6 alkenyl or $C_2$-6 alkynyl each optionally substituted by one or more groups independently selected from halo, —CN, —N($R^{a2}$)$R^{b2}$, —O$R^{c2}$, —S$R^{d2}$ and =O;
each $R^{a2}$, $R^{b2}$, $R^{c2}$ and $R^{d2}$ independently represents H or $C_{1-6}$ alkyl, $C_{2-6}$ alkenyl or $C_{2-6}$ alkynyl each optionally substituted by one or more fluoro;
each Y independently represents halo, $R^{a3}$, —CN, N(H)—C(O)$R^{b3}$, —C(O)O$R^{e3}$, —N(H)—S(O)$_2$$R^{f3}$, —S(O)$_2$$R^{f3}$, —N(H)—S(O)$_q$N($R^{g3}$)$R^{h3}$, —C(O)CH$_3$, —N$_3$, —N($R^{j3}$)$R^{k3}$, —N(H)CH, —NO$_2$, —ONO$_2$, —O$R^{l3}$, —S$R^{m3}$ or =O;
each $R^{a3}$ and $R^{f3}$ independently represents $C_{1-6}$ alkyl, $C_{2-6}$ alkenyl or $C_{2-6}$ alkynyl each optionally substituted by one or more groups independently selected from halo, —CN, —N($R^{j4}$)$R^{k4}$, —O$R^{l4}$, —S$R^{m4}$ and =O;
each $R^{b3}$, $R^{e3}$, $R^{g3}$, $R^{h3}$, $R^{j3}$, $R^{k3}$, $R^{l3}$ and $R^{m3}$ independently represents H or $C_{1-6}$ alkyl, $C_{2-6}$ alkenyl or $C_{2-6}$ alkynyl each optionally substituted by one or more groups independently selected from halo —CN, —N(R$^{j4}$)R$^{k4}$, —OR$^{l4}$, —SR$^{m4}$ and =O;

each R$^{j4}$, R$^{k4}$, R$^{l4}$, and R$^{m4}$, independently represents H or C$_{1-6}$ alkyl, C$_{2-6}$ alkenyl or C$_{2-6}$ alkynyl each optionally substituted by one or more groups independently selected from halo —CN or =O; and each p and q independently represents 1 or 2, but with the provisos that the compound of formula I does not represent:

(A)

3-nitro-2-(piperidin-4-ylsulfonyl)pyridine, tert-butyl 3-((3-nitropyridin-2-yl)sulfonyl)pyrrolidine-1-carboxylate, tert-butyl (R)-3-((3-nitropyridin-2-yl)sulfonyl)pyrrolidine-1-carboxylate, tert-butyl (S)-3-((3-nitropyridin-2-yl)sulfonyl)pyrrolidine-1-carboxylate, tert-butyl 3-((3-nitropyridin-2-yl)sulfonyl)piperidine-1-carboxylate, and tert-butyl 4-((3-nitropyridin-2-yl)sulfonyl)piperidine-1-carboxylate;

and (B)

3-nitro-2-(4-piperidinylsulfinyl)-pyridine, 3-nitro-2-(3-pyrrolidinylsulfinyl)-pyridine, 3-nitro-2-(3-piperidinylsulfinyl)-pyridine, 4-[(3-nitro-2-pyridinyl)sulfinyl]-1-piperidinecarboxylic acid 1,1-dimethylethyl ester, 3-[(3-nitro-2-pyridinyl)sulfinyl]-1-pyrrolidinecarboxylic acid 1,1-dimethylethyl ester, and 3-[(3-nitro-2-pyridinyl)sulfinyl]-1-piperidinecarboxylic acid 1,1-dimethylethyl ester.

2. A compound as claimed in claim 1, wherein each Y independently represents halo, R$^{a3}$, —N(H)—C(O)R$^{b3}$, —C(O)OR$^{e3}$, —N(H)—S(O)$_2$R$^{f3}$, —N(H)—S(O)$_q$N(R$^{g3}$)R$^{h3}$, —N(R$^{j3}$)R$^{k3}$ or —OR$^{l3}$.

3. A compound as claimed in claim 1, wherein each Y independently represents methyl or —C(O)CH$_3$.

4. A compound as claimed in claim 1, wherein each R$^1$, R$^2$ and R$^3$ each independently represents H, halo, —N(R$^{j1}$)R$^{k1}$ or —OR$^{l1}$.

5. A compound as claimed in claim 1, wherein each R$^{a1}$, R$^{j1}$, R$^{k1}$, R$^{i1}$ and R$^{ml}$ independently represent C$_{1-6}$ alkyl, C$_{2-6}$ alkenyl or C$_{1-6}$ alkynyl optionally substituted by one or more fluoro.

6. A compound as claimed in claim 1, wherein each R$^1$, R$^2$ and R$^3$ independently represents H, halo, —N(R$^{j1}$)R$^{k1}$ or —OR$^{l1}$.

7. A compound as claimed in claim 1, wherein each R$^{a1}$, R$^{j1}$, R$^{k1}$, R$^{i1}$ and R$^{ml}$ independently represent C$_{1-6}$ alkyl optionally substituted by one or more fluoro.

8. A compound as claimed in claim 1, wherein R$^1$, R$^2$ and R$^3$ each independently represent H or —OR$^{l1}$.

9. A compound as claimed in claim 1, wherein:

each R$^1$, R$^2$ and R$^3$ each independently represent H or —OR$^{l1}$; and each R$^{l1}$ independently represents C$_{1-6}$ alkyl optionally substituted by one or more fluoro.

10. A compound as claimed in claim 1, wherein R$^1$ represents —OCH$_3$.

11. A method of treating cancer comprising administering to a patient in need thereof a therapeutically effective amount of a compound, wherein the cancer is selected from the group consisting of glioblastoma, pharyngeal squamous cell carcinoma, colorectal carcinoma, epidermoid (skin) carcinoma, pancreatic ductal carcinoma, metastatic mammary adenocarcinoma, lung carcinoma, leukemia, non-small cell lung cancer, colon cancer, melanoma, ovarian cancer, renal cancer, prostate cancer, and; and wherein the compound is represented by formula I or a pharmaceutically acceptable salt thereof, wherein:

L represents —S(O)$_n$—;

n represents 2 or 1;

X represents a 5- or 6-membered non-aromatic heterocyclyl, connected to L via a carbon atom, and optionally substituted by one or more groups independently selected from Y;

R$^1$, R$^2$ and R$^3$ each independently represent H, halo, R$^{a1}$, —CN, C(O)R$^{b1}$, —C(S)R$^{b1}$, —C(NR$^{n1}$)R$^{b1}$, —C(N(OR$^{o1}$))R$^{b1}$, —N(R$^{p1}$)—C(S)R$^{b1}$, N(R$^{p1}$)—C(NR$^{n1}$)R$^{b1}$, —N(R$^{P1}$)—C(N(OR$^{o1}$))R$^{b1}$, —O—C(O)R$^{b1}$, —O—C(S)R$^{b1}$, —O—C(NR$^{n1}$)R$^{b1}$, —O—C(N(OR$^{o1}$))R$^{b1}$, —C(O)N(R$^{c1}$)R$^{d1}$, —C(S)N(R$^{c1}$)R$^{d1}$, —C(NR$^{n1}$)N(R$^{c1}$)R$^{d1}$, —C(N(OR$^{o1}$))N(R$^{c1}$)R$^{d1}$, —N(R$^{p1}$)—C(O)N(R$^{c1}$)R$^{d1}$, —N(R$^{p1}$)—C(S)N(R$^{c1}$)R$^{d1}$, —N(R$^{p1}$)—C(NR$^{n1}$)N(R$^{c1}$)R$^{d1}$, —N(R$^{p1}$)—C(N(OR$^{o1}$))N(R$^{c1}$)R$^{d1}$, —O—C(O)N(R$^{c1}$)R$^{d1}$, —O—C(S)N(R$^{c1}$)R$^{d1}$, —O—C(NR$^{n1}$)N(R$^{c1}$)R$^{d1}$, —O—C(N(OR$^{o1}$))N(R$^{c1}$)R$^{d1}$, —C(O)OR$^{e1}$, —C(S)OR$^{e1}$, —C(NR$^{n1}$)OR$^{e1}$, —C(N(OR$^{o1}$))OR$^{e1}$, —N(R$^{p1}$)—C(O)OR$^{e1}$, —N(R$^{p1}$)—C(S)OR$^{e1}$, —N(R$^{p1}$)—C(NR$^{n1}$)OR$^{e1}$, —N(R$^{p1}$)—C(N(OR$^{o1}$))OR$^{e1}$, —O—C(O)OR$^{e1}$, —O—C(S)OR$^{e1}$, —O—C(NR$^{n1}$)OR$^{e1}$, —O—C(N(OR$^{o1}$))OR$^{e1}$, —S(O)$_p$R$^{f1}$, —N(R$^{p1}$)—S(O)$_p$R$^{f1}$, —O—S(O)$_p$R$^{f1}$, —S(O)$_p$N(R$^{g1}$)R$^{h1}$, —N(R$^{p1}$)—S(O)$_p$N(R$^{g1}$)R$^{h1}$, —O—S(O)$_p$N(R$^{g1}$)R$^{h1}$, —S(O)$_p$OR$^{i1}$, —N(R$^{p1}$)—S(O)$_p$OR$^{i1}$, —O—S(O)$_p$OR$^{i1}$, —N$_3$, —N(R$^{j1}$)R$^{k1}$, —N(H)CN, —NO$_2$, —ONO$_2$, —OR$^{l1}$ or —SR$^{ml}$;

each R$^{a1}$ and R$^{f1}$ independently represents C$_{1-6}$ alkyl, C$_{2-6}$ alkenyl or C$_{2-6}$ alkynyl each optionally substituted by one or more groups independently selected from halo, —CN, —N(R$^{a2}$)R$^{b2}$, —OR$^{c2}$, —SR$^{d2}$ and =O;

each R$^{b1}$, R$^{c1}$, R$^{d1}$, R$^{e1}$, R$^{f1}$, R$^{g1}$, R$^{h1}$, R$^{i1}$, R$^{j1}$, R$^{k1}$, R$^{l1}$, R$^{m1}$, R$^{n1}$, R$^{o1}$, R$^{b1}$, independently represents H or C$_1$-6 alkyl, C$_2$-6 alkenyl or C$_2$-6 alkynyl each optionally substituted by one or more groups independently selected from halo, —CN, —N(R$^{a2}$)R$^{b2}$, —OR$^{c2}$, —SR$^{d2}$ and =O;

each R$^{a2}$, R$^{b2}$, R$^{c2}$ and R$^{d2}$ independently represents H or C$_{1-6}$ alkyl, C$_{2-6}$ alkenyl or C$_{2-6}$ alkynyl each optionally substituted by one or more fluoro;

each Y independently represents halo, R$^{a3}$, —CN, N(H)—C(O)R$^{b3}$, —C(O)OR$^{e3}$, —N(H)—S(O)$_2$R$^{f3}$, —N(H)—S(O)$_q$N(R$^{g3}$)R$^{h3}$, —C(O)CH$_3$, —N$_3$(R$^{j3}$)R$^{k3}$, —N(H)CH, —NO$_2$, —ONO$_2$, —OR$^{l3}$, —SR$^{m3}$ or =O;

each R$^{a3}$ and R$^{f3}$ independently represents C$_{1-6}$ alkyl, C$_{2-6}$ alkenyl or C$_{2-6}$ alkynyl each optionally substituted by one or more groups independently selected from halo, —CN, —N(R$^{j4}$)R$^{k4}$, —OR$^{i4}$, —SR$^{m4}$ and =O;

each $R^{b3}$, $R^{e3}$, $R^{g3}$, $R^{h3}$, $R^{j3}$, $R^{k3}$, $R^{l3}$ and $R^{m3}$, independently represents H or $C_{1-6}$ alkyl, $C_{2-6}$ alkenyl or $C_{2-6}$ alkynyl each optionally substituted by one or more groups independently selected from halo —CN, —N($R^{j4}$)$R^{k4}$, —OR$^{l4}$, —SR$^{m4}$ and =O, each $R^{j4}$, $R^{k4}$, $R^{l4}$, and $R^{m4}$ independently represents H or $C_{1-6}$ alkyl, $C_{2-6}$ alkenyl or $C_{2-6}$ alkynyl each optionally substituted by one or more groups independently selected from halo —CN or =O each p and q independently represents 1 or 2.

12. A pharmaceutical composition comprising a compound, and one or more pharmaceutically acceptable adjuvant, diluent and/or carrier, wherein the compound is represented by formula I

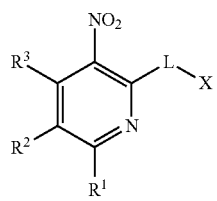

(I)

or a pharmaceutically acceptable salt thereof, wherein:
L represents —S(O)$_n$—;
n represents 2 or 1;
X represents a 5- or 6-membered non-aromatic heterocyclyl, connected to L via a carbon atom, and optionally substituted by one or more groups independently selected from Y;
$R^1$, $R^2$ and $R^3$ each independently represent H, halo, $R^{a1}$, —CN, C(O)$R^{b1}$, —C(S)$R^{b1}$, —C(NR$^{n1}$)$R^{b1}$, —C(N(OR$^{o1}$))$R^{b1}$, —N($R^{P1}$)—C(S)$R^{b1}$, —N($R^{P1}$)—C(NR$^{n1}$)$R^{b1}$, —N($R^{P1}$)—C(N(OR$^{o1}$))$R^{b1}$, —O—C(O)$R^{b1}$, —O—C(S)$R^{b1}$, —O—C(NR$^{n1}$)$R^{b1}$, —O—C(N(OR$^{o1}$))$R^{b1}$, —C(O)N($R^{c1}$)$R^{d1}$, —C(S)N($R^{c1}$)$R^{d1}$, —C(NR$^{n1}$)N($R^{c1}$)$R^{d1}$, —C(N(OR$^{o1}$))N($R^{c1}$)$R^{d1}$, —N($R^{P1}$)—C(O)N($R^{c1}$)$R^{d1}$, —N($R^{P1}$)—C(S)N($R^{c1}$)$R^{d1}$, —N($R^{P1}$)—C(NR$^{n1}$)N($R^{c1}$)$R^{d1}$, —N($R^{P1}$)—C(N(OR$^{o1}$))N($R^{c1}$)$R^{d1}$, —O—C(O)N($R^{c1}$)$R^{d1}$, —O—C(S)N($R^{c1}$)$R^{d1}$, —O—C(NR$^{n1}$)N($R^{c1}$)$R^{d1}$, —O—C(N(OR$^{o1}$))N($R^{c1}$)$R^{d1}$, —C(O)OR$^{e1}$, —C(S)OR$^{e1}$, —C(NR$^{n1}$)OR$^{e1}$, —C(N(OR$^{o1}$))OR$^{e1}$, —N($R^{P1}$)—C(O)OR$^{e1}$, —N($R^{P1}$)—C(S)OR$^{e1}$, —N($R^{P1}$)—C(NR$^{n1}$)OR$^{e1}$, —N($R^{P1}$)—C(N(OR$^{o1}$))OR$^{e1}$, —O—C(O)OR$^{e1}$, —O—C(S)OR$^{e1}$, —O—C(NR$^{n1}$)OR$^{e1}$, —O—C(N(OR$^{o1}$))OR$^{e1}$, —S(O)$_p$R$^{f1}$, —N($R^{P1}$)—S(O)$_p$R$^{f1}$, —O—S(O)$_p$R$^{f1}$, —S(O)$_p$N($R^{g1}$)$R^{h1}$, —N($R^{P1}$)—S(O)$_p$N($R^{g1}$)$R^{h1}$, —O—S(O)$_p$N($R^{g1}$)$R^{h1}$, —S(O)$_p$OR$^{i1}$, —N($R^{P1}$)—S(O)$_p$OR$^{i1}$, —O—S(O)$_p$OR$^{i1}$, —N$_3$, —N($R^{j1}$)$R^{k1}$, —N(H)CN, —NO$_2$, —ONO$_2$, —OR$^{l1}$ or —SR$^{ml}$;

each $R^{a1}$ and $R^{f1}$ independently represents $C_{1-6}$ alkyl, $C_{2-6}$ alkenyl or $C_{2-6}$ alkynyl each optionally substituted by one or more groups independently selected from halo, —CN, —N($R^{a2}$)$R^{b2}$, —OR$^{c2}$, —SR$^{d2}$ and =O each $R^{b1}$, $R^{c1}$, $R^{d1}$, $R^{e1}$, $R^{g1}$, $R^{h1}$, $R^{i1}$, $R^{j1}$, $R^{k1}$, $R^{l1}$, $R^{m1}$, $R^{n1}$, $R^{o1}$, and $R^{p1}$ independently represents H or $C_{1-6}$ alkyl, $C_{2-6}$ alkenyl or $C_{2-6}$ alkynyl each optionally substituted by one or more groups independently selected from halo, —CN, —N($R^{a2}$)$R^{b2}$, —OR$^{c2}$, —SR$^{d2}$ and =O;

each $R^{a2}$, $R^{b2}$, $R^{c2}$ and $R^{d2}$ independently represents H or $C_{1-6}$ alkyl, $C_{2-6}$ alkenyl or $C_{2-6}$ alkynyl each optionally substituted by one or more fluoro;

each Y independently represents halo, $R^{a3}$, —CN, N(H)—C(O)$R^{b3}$, —C(O)OR$^{e3}$, —N(H)—S(O)$_2$R$^{f3}$, —N(H)—S(O)$_q$N($R^{g3}$)$R^{h3}$, —C(O)CH$_3$, —N$_3$($R^{j3}$) $R^{k3}$, —N(H)CH, —NO$_2$, —ONO$_2$, —OR$^{l3}$, —SR$^{m3}$ or =O;

each $R^{a1}$ and $R^{f1}$ independently represents $C_{1-6}$ alkyl, $C_{2-6}$ alkenyl or $C_{2-6}$ alkynyl each optionally substituted by one or more groups independently selected from halo, —CN, —N($R^{a2}$)$R^{b2}$, —OR$^{c2}$, —SR$^{d2}$ and =O each $R^{b3}$, $R^{e3}$, $R^{g3}$, $R^{h3}$, $R^{j3}$, $R^{k3}$, $R^{l3}$, and $R^{m3}$, independently represents H or $C_{1-6}$ alkyl, $C_{2-6}$ alkenyl or $C_{2-6}$ alkynyl each optionally substituted by one or more groups independently selected from halo —CN, —N($R^{j4}$)$R^{k4}$, —OR$^{l4}$, —SR$^{m4}$ and =O each $R^{j4}$, $R^{k4}$, $R^{l4}$, and $R^{m4}$ independently represents H or $C_{1-6}$ alkyl, $C_{2-6}$ alkenyl or $C_{2-6}$ alkynyl each optionally substituted by one or more groups independently selected from halo —CN or =O each p and q independently represents 1 or 2.

13. A combination product comprising:
(a) a compound; and
(b) one or more other therapeutic agent that is useful in the treatment of cancer, wherein each of components (A) and (B) is formulated in admixture, with one or more a pharmaceutically-acceptable adjuvant, diluent or carrier; wherein the cancer is selected from the group consisting of glioblastoma, pharyngeal squamous cell carcinoma, colorectal carcinoma, epidermoid (skin) carcinoma, pancreatic ductal carcinoma, metastatic mammary adenocarcinoma, lung carcinoma, leukemia, non-small cell lung cancer, colon cancer, melanoma, ovarian cancer, renal cancer, prostate cancer, and breast cancer; and wherein the compound is represented by formula I

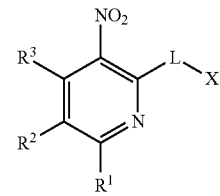

(I)

or a pharmaceutically acceptable salt thereof, wherein:
L represents —S(O)$_n$—;
n represents 2 or 1;
X represents a 5- or 6-membered non-aromatic heterocyclyl, connected to L via a carbon atom, and optionally substituted by one or more groups independently selected from Y;
$R^1$, $R^2$ and $R^3$ each independently represent H, halo, $R^{a1}$, —CN, C(O)$R^{b1}$, —C(S)$R^{b1}$, —C(NR$^{n1}$)$R^{b1}$, —C(N(OR$^{o1}$))$R^{b1}$, —N($R^{P1}$)—C(S)$R^{b1}$, —N($R^{P1}$)—C(NR$^{n1}$)$R^{b1}$, —N($R^{P1}$)—C(N(OR$^{o1}$))$R^{b1}$, —O—C(O)$R^{b1}$, —O—C(S)$R^{b1}$, —O—C(NR$^{n1}$)$R^{b1}$, —O—C(N(OR$^{o1}$))$R^{b1}$, —C(O)N($R^{c1}$)$R^{d1}$, —C(S)N($R^{c1}$)$R^{d1}$, —C(NR$^{n1}$)N($R^{c1}$)$R^{d1}$, —C(N(OR$^{o1}$))N($R^{c1}$)$R^{d1}$, —N($R^{P1}$)—C(O)N($R^{c1}$)$R^{d1}$, —N($R^{P1}$)—C(S)N($R^{c1}$)$R^{d1}$, —N($R^{P1}$)—C(NR$^{n1}$)N($R^{c1}$)$R^{d1}$, —N($R^{P1}$)—C(N(OR$^{o1}$))N($R^{c1}$)$R^{d1}$, —O—C(O)N($R^{c1}$)$R^{d1}$, —O—C(S)N($R^{c1}$)$R^{d1}$, —O—C(NR$^{n1}$)N($R^{c1}$)$R^{d1}$, —O—C(N (OR$^{o1}$))N(R$^{c1}$)R$^{d1}$, —C(O)OR$^{e1}$, —C(S)OR$^{e1}$, —C(NR$^{n1}$)OR$^{e1}$, —C(N(OR$^{o1}$))OR$^{e1}$, —N(R$^{p1}$)—C(O)OR$^{e1}$, —N(R$^{p1}$)—C(S)OR$^{e1}$, —N(R$^{p1}$)—C(NR$^{n1}$)OR$^{e1}$, —N(R$^{p1}$)—C(N(OR$^{o1}$))OR$^{e1}$, —O—C(O)OR$^{e1}$, —O—C(S)OR$^{e1}$, —O—C(NR$^{n1}$)OR$^{e1}$, —O—C(N(OR$^{o1}$))OR$^{e1}$, —S(O)$_p$R$^{f1}$, —N(R$^{p1}$)—S(O)$_p$R$^{f1}$, —O—S(O)$_p$R$^{f1}$, —S(O)$_p$N(R$^{g1}$)R$^{h1}$, —N(R$^{p1}$)—S(O)$_p$N(R$^{g1}$)R$^{h1}$, —O—S(O)$_p$N(R$^{g1}$)R$^{h1}$, —S(O)$_p$OR$^{i1}$, —N(R$^{p1}$)—S(O)$_p$OR$^{i1}$, —O—S(O)$_p$OR$^{i1}$, —N$_3$, —N(R$^{j1}$)R$^{k1}$, —N(H)CN, —NO$_2$, —ONO$_2$, —OR$^{l1}$ or —SR$^{m1}$;

each R$^{a1}$ and R$^{f1}$ independently represents C$_{1-6}$ alkyl, C$_{2-6}$ alkenyl or C$_{2-6}$ alkynyl each optionally substituted by one or more groups independently selected from halo, —CN, —N(R$^{a2}$)R$^{b2}$, —OR$^{c2}$, —SR$^{d2}$ and =O each R$^{b1}$, R$^{c1}$, R$^{d1}$, R$^{e1}$, R$^{g1}$, R$^{h1}$, R$^{i1}$, R$^{j1}$, R$^{k1}$, R$^{l1}$, R$^{m1}$, R$^{n1}$, R$^{o1}$, and R$^{p1}$ independently represents H or C$_{1-6}$ alkyl, C$_{2-6}$ alkenyl or C$_{2-6}$ alkynyl each optionally substituted by one or more groups independently selected from halo, —CN, —N(R$^{a2}$)R$^{b2}$, —OR$^{c2}$, —SR$^{d2}$ and =O each R$^{a2}$, R$^{b2}$, R$^{c2}$ and R$^{d2}$ independently represents H or C$_{1-6}$ alkyl, C$_{2-6}$ alkenyl or C$_{2-6}$ alkynyl each optionally substituted by one or more fluoro;

each Y independently represents halo, R$^{a3}$, —CN, N(H)—C(O)R$^{b3}$, —C(O)OR$^{e3}$, —N(H)—S(O)$_2$R$^{f3}$, —N(H)—S(O)$_q$N(R$^{g3}$)R$^{h3}$, —C(O)CH$_3$, —N$_3$(R$^{j3}$)R$^{k3}$, —N(H)CH, —NO$_2$, —ONO$_2$, —OR$^{l3}$, —SR$^{m3}$ or =O;

each R$^{a3}$ and R$^{f3}$ independently represents C$_{1-6}$ alkyl, C$_{2-6}$ alkenyl or C$_{2-6}$ alkynyl each optionally substituted by one or more groups independently selected from halo, —CN, —N(R$^{j4}$)R$^{k4}$, —OR$^{l4}$, —SR$^{m4}$ and =O;

each R$^{b3}$, R$^{e3}$, R$^{g3}$, R$^{h3}$, R$^{j3}$, R$^{k3}$, R$^{l3}$, and R$^{m3}$, independently represents H or C$_{1-6}$ alkyl, C$_{2-6}$ alkenyl or C$_{2-6}$ alkynyl each optionally substituted by one or more groups independently selected from halo —CN, —N(R$^{j4}$)R$^{k4}$, —OR$^{l4}$, —SR$^{m4}$ and =O each R$^{j4}$, R$^{k4}$, R$^{l4}$, and R$^{m4}$ independently represents H or C$_{1-6}$ alkyl, C$_{2-6}$ alkenyl or C$_{2-6}$ alkynyl each optionally substituted by one or more groups independently selected from halo —CN or =O each p and q independently represents 1 or 2.

14. A kit-of-parts comprising:

(a) a pharmaceutical composition as defined in claim 12; and (b) one or more other therapeutic agent that is useful in the treatment of cancer, in admixture with one or more pharmaceutically-acceptable adjuvant, diluent or carrier, which components (a) and (b) are each provided in a form that is suitable for administration in conjunction with the other, wherein the cancer is selected from the group consisting of glioblastoma, pharyngeal squamous cell carcinoma, colorectal carcinoma, epidermoid (skin) carcinoma, pancreatic ductal carcinoma, metastatic mammary adenocarcinoma, lung carcinoma, leukemia, non-small cell lung cancer, colon cancer, melanoma, ovarian cancer, renal cancer, and prostate cancer.

15. A process for the preparation of a compound as defined in claim 1, which process comprises:

(i) where n represents 2, reaction of a compound of formula IIA

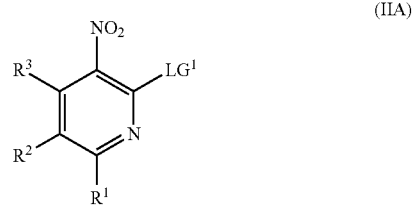

(IIA)

wherein R$^1$, R$^2$ and R$^3$ are as defined in claim 1 and LG$^1$ represents a suitable leaving group, with a compound of formula IIIA

(IIIA)

X is as defined in claim 1 and M represents an alkali metal ion, in the presence of a suitable acid and in the presence of a suitable solvent, and optionally in the presence of a suitable phase transfer catalyst;

(ii) where n represents 2, reaction of a compound of formula IIB

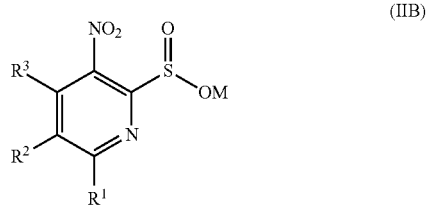

(IIB)

wherein R$^1$, R$^2$ and R$^3$ are as defined in claim 1 and LG$^1$ represents a suitable leaving group, with a compound of formula IIIB

(IIIB)

wherein X is as defined in claim 1 and LG$^2$ represents a suitable leaving group, in the presence of a suitable acid and in the presence of a suitable solvent, and optionally in the presence of a suitable phase transfer catalyst;

(iii) reaction of a compound of formula IIA with a compound of formula IIIA, in the presence of a suitable metal halide and in the presence of a suitable solvent;

(iv) where n represents 2, reaction of a compound of formula IIB with a compound of formula IIIB, in the presence of a suitable metal halide and in the presence of a suitable solvent;

(v) reaction of a compound of formula IV

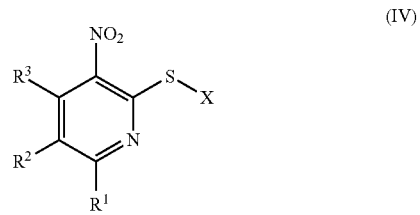

(IV)

wherein R¹ to R³ and X are as defined in claim 1, with a suitable oxidising agent in the presence of a suitable solvent, and optionally in the presence of water;
or
(vi) where n represents 2, reaction of a compound of formula V

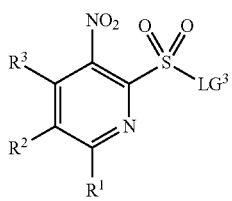 (V)

wherein R¹, R² and R³ are as defined in claim 1 and LG³ represents a suitable leaving group with a compound of formula VI

 (VI)

wherein X is as defined in claim 1, in the presence of a suitable Lewis acid and in the presence of a suitable solvent.

* * * * *

UNITED STATES PATENT AND TRADEMARK OFFICE
CERTIFICATE OF CORRECTION

PATENT NO. : 11,168,069 B2
APPLICATION NO. : 16/483961
DATED : November 9, 2021
INVENTOR(S) : Benjamin Pelcman et al.

It is certified that error appears in the above-identified patent and that said Letters Patent is hereby corrected as shown below:

In the Claims

At Column 34, Claim number 1, Line numbers 24 and 25, delete "-N($R^{P1}$)-C(N$R^{n1}$)$R^{b1}$" and replace with -- -N($R^{p1}$)-C(N$R^{n1}$)$R^{b1}$ --.

At Column 34, Claim number 1, Line number 25, delete "N($R^{P1}$)-C(N(O$R^{o1}$))$R^{b1}$" and replace with -- N($R^{p1}$)-C(N(O$R^{o1}$))$R^{b1}$ --.

At Column 34, Claim number 1, Line number 43, delete "S$R^{m1}$" and replace with -- S$R^{m1}$ --.

At Column 34, Claim number 1, Line number 49, delete "$R^{b1}$" and replace with -- $R^{p1}$ --.

At Column 34, Claim number 1, Line numbers 49 and 50, delete "$C_{1-6}$ alkyl, $C_{2-6}$ alkenyl or $C_{2-6}$ alkynyl" and replace with -- $C_{1-6}$ alkyl, $C_{2-6}$ alkenyl or $C_{2-6}$ alkynyl --.

At Column 35, Claim number 7, Line number 51, delete "S$R^{m1}$" and replace with -- S$R^{m1}$ --.

At Column 36, Claim number 11, Line number 27, delete "N($R^{P1}$)-C(N(O$R^{o1}$))$R^{b1}$" and replace with -- N($R^{p1}$)-C(N(O$R^{o1}$))$R^{b1}$ --.

At Column 36, Claim number 11, Line number 45, delete "S$R^{m1}$" and replace with -- S$R^{m1}$ --.

At Column 36, Claim number 11, Line number 51, delete "$R^{b1}$" and replace with -- $R^{p1}$ --.

At Column 36, Claim number 11, Line numbers 51 and 52, delete "$C_{1-6}$ alkyl, $C_{2-6}$ alkenyl or $C_{2-6}$ alkynyl" and replace with -- $C_{1-6}$ alkyl, $C_{2-6}$ alkenyl or $C_{2-6}$ alkynyl --.

At Column 37, Claim number 12, Line numbers 36 and 37, delete "-N($R^{P1}$)-C(N$R^{n1}$)$R^{b1}$" and replace with -- -N($R^{p1}$)-C(N$R^{n1}$)$R^{b1}$ --.

Signed and Sealed this
Twenty-first Day of February, 2023

*Katherine Kelly Vidal*

Katherine Kelly Vidal
*Director of the United States Patent and Trademark Office*

CERTIFICATE OF CORRECTION (continued)
U.S. Pat. No. 11,168,069 B2

At Column 37, Claim number 12, Line number 37, delete "N($R^{P1}$)-C(N(O$R^{o1}$))$R^{b1}$" and replace with -- N($R^{p1}$)-C(N(O$R^{o1}$))$R^{b1}$ --.

At Column 37, Claim number 12, Line number 56, delete "S$R^{m1}$" and replace with -- S$R^{m1}$ --.

At Column 38, Claim number 13, Line numbers 59 and 60, delete "-N($R^{P1}$)-C(N$R^{n1}$)$R^{b1}$" and replace with -- -N($R^{p1}$)-C(N$R^{n1}$)$R^{b1}$ --.

At Column 38, Claim number 13, Line number 60, delete "N($R^{P1}$)-C(N(O$R^{o1}$))$R^{b1}$" and replace with -- N($R^{p1}$)-C(N(O$R^{o1}$))$R^{b1}$ --.

At Column 39, Claim number 13, Line number 11, delete "S$R^{m1}$" and replace with -- S$R^{m1}$ --.